US010295821B2

(12) United States Patent
McCabe

(10) Patent No.: US 10,295,821 B2
(45) Date of Patent: May 21, 2019

(54) LAMINATED LENSES WITH ANTI-FOGGING FUNCTIONALITY

(71) Applicant: Oakley, Inc., Foothill Ranch, CA (US)

(72) Inventor: Brock Scott McCabe, Laguna Niguel, CA (US)

(73) Assignee: Oakley, Inc., Foothill Ranch, CA (US)

(*) Notice: Subject to any disclaimer, the term of this patent is extended or adjusted under 35 U.S.C. 154(b) by 0 days.

(21) Appl. No.: 15/679,872

(22) Filed: Aug. 17, 2017

(65) Prior Publication Data

US 2018/0052319 A1 Feb. 22, 2018

Related U.S. Application Data

(60) Provisional application No. 62/377,478, filed on Aug. 19, 2016.

(51) Int. Cl.
*G02C 11/08* (2006.01)
*G02B 27/00* (2006.01)
(Continued)

(52) U.S. Cl.
CPC .......... *G02B 27/0006* (2013.01); *A61F 9/029* (2013.01); *G02B 1/18* (2015.01); *G02C 11/08* (2013.01); *A61F 9/028* (2013.01); *B29D 11/0073* (2013.01); *G02C 7/02* (2013.01); *G02C 7/101* (2013.01); *G02C 7/102* (2013.01); *G02C 7/108* (2013.01); *G02C 2202/16* (2013.01)

(58) Field of Classification Search
CPC ............................ G02C 2202/16; G02C 11/08
USPC .............................................. 351/62, 159.62
See application file for complete search history.

(56) References Cited

U.S. PATENT DOCUMENTS 5,353,148 A   10/1994   Eid et al.
5,471,036 A   11/1995   Sperbeck
(Continued)

FOREIGN PATENT DOCUMENTS

CN   204 378 029 U   6/2015
EP       1460473 B1   8/2007
(Continued)

OTHER PUBLICATIONS

Extended European Search Report issued in counterpart European Patent Application No. EP 17 18 6801, dated Feb. 7, 2018.
(Continued)

*Primary Examiner* — Hung X Dang
(74) *Attorney, Agent, or Firm* — Sterne, Kessler, Goldstein & Fox P.L.L.C.

(57) ABSTRACT

Eyewear can include a laminated lens that has anti-fogging functionality. The lens can include an anti-fog layer configured to resist accumulation of condensate on a posterior surface of the lens and an interface layer comprising a thin layer of inorganic material with ceramic bulk properties. The interface layer can be disposed between the anti-fog layer and an adhesive layer configured to adhere to adjacent layers of the laminated lens. The adhesive layer can be disposed between two lens elements. One of the lens elements can include a polymer layer that provides stiffness to the lens and an electrically conductive layer deposited on the polymer layer. When electric current is applied across the electrically conductive layer via one or more electrodes, the lens can be heated.

33 Claims, 15 Drawing Sheets

(51) Int. Cl.
*A61F 9/02* (2006.01)
*G02B 1/18* (2015.01)
*G02C 7/10* (2006.01)
*G02C 7/02* (2006.01)
*B29D 11/00* (2006.01)

(56) References Cited

U.S. PATENT DOCUMENTS

| | | |
|---|---|---|
| 6,178,034 B1 | 1/2001 | Allemand et al. |
| 6,908,698 B2 | 6/2005 | Yoshida et al. |
| 6,995,891 B2 | 2/2006 | Agrawal et al. |
| 7,277,215 B2 | 10/2007 | Greer |
| 7,808,692 B2 | 10/2010 | Karmhag et al. |
| 8,177,358 B2 | 5/2012 | Matera et al. |
| 8,398,234 B2 | 3/2013 | Wang et al. |
| 8,687,261 B2 | 4/2014 | Gillaspie et al. |
| 8,746,879 B2 * | 6/2014 | Jiang .............. B29D 11/0073 351/159.42 |
| 9,134,547 B2 | 9/2015 | McCabe et al. |
| 9,383,594 B2 | 7/2016 | McCabe et al. |
| 2003/0129422 A1 | 7/2003 | Shirakawa et al. |
| 2011/0126345 A1 | 6/2011 | Matsumoto et al. |
| 2012/0137398 A1 | 6/2012 | Arnold |
| 2012/0137414 A1 | 6/2012 | Saylor |
| 2013/0235452 A1 | 9/2013 | You et al. |
| 2015/0272260 A1 | 10/2015 | Ryan et al. |
| 2015/0277146 A1 | 10/2015 | Crespo Vazquez et al. |
| 2015/0286073 A1 | 10/2015 | Blum |
| 2015/0362817 A1 | 12/2015 | Patterson et al. |
| 2015/0374550 A1 | 12/2015 | Saylor |
| 2016/0033837 A1 | 2/2016 | Bjornard et al. |
| 2016/0048037 A1 | 2/2016 | McCabe et al. |
| 2016/0334644 A1 | 11/2016 | Garofolo et al. |

FOREIGN PATENT DOCUMENTS

| | | |
|---|---|---|
| GB | 2522389 A | 7/2015 |
| WO | WO 2013169987 A1 | 11/2013 |
| WO | WO 2016054198 A1 | 4/2016 |
| WO | WO 2016077431 A2 | 5/2016 |
| WO | WO 2016145064 A1 | 9/2016 |

OTHER PUBLICATIONS

New dual layer cellulose acetate anti fog lens rimless fashionable snow goggles (http://hubosports.en.alibaba.com/product/60119246566-215413686/New_dual_layer_cellulose_acetate_anti_fog_lens_rimless_fashionable_snow_goggles.html).

* cited by examiner

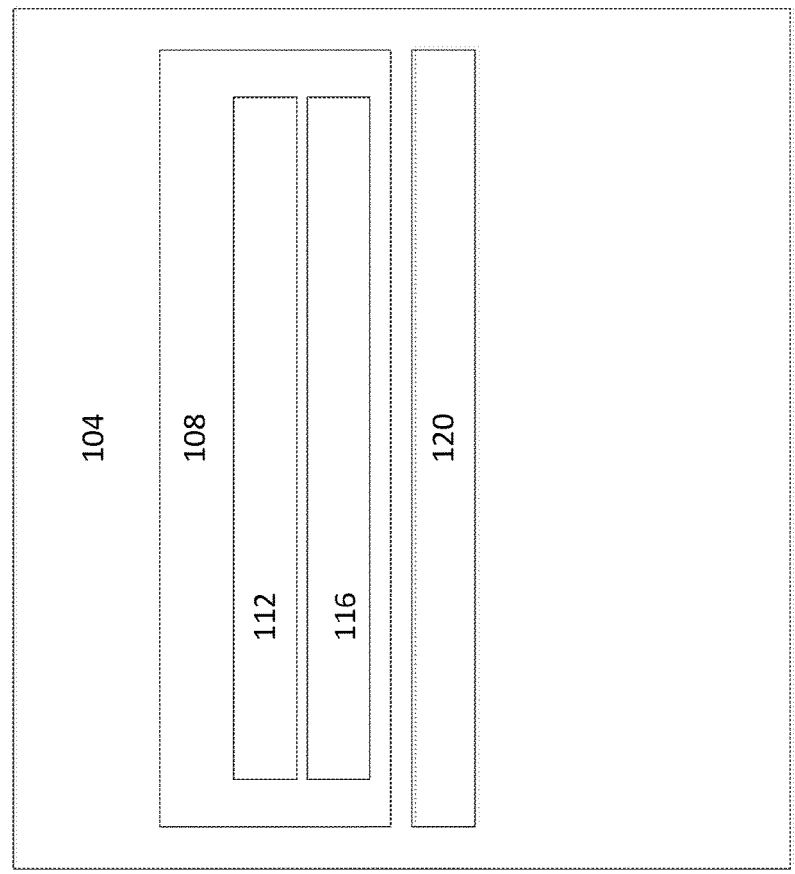
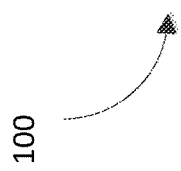
FIG. 1A

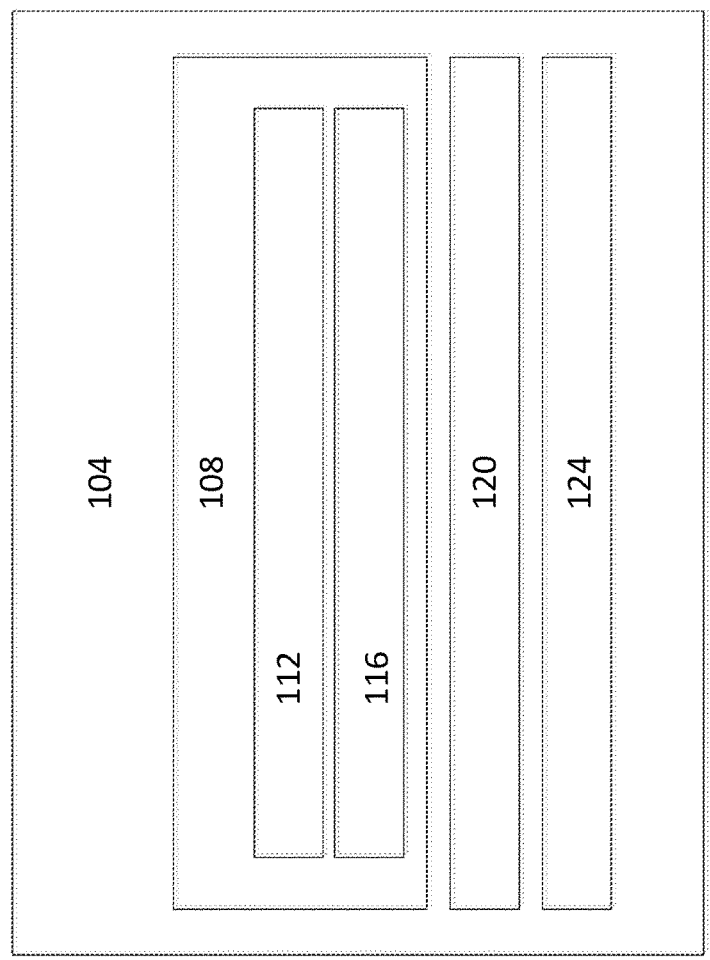
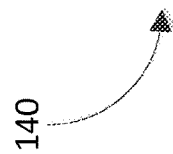
FIG. 1B

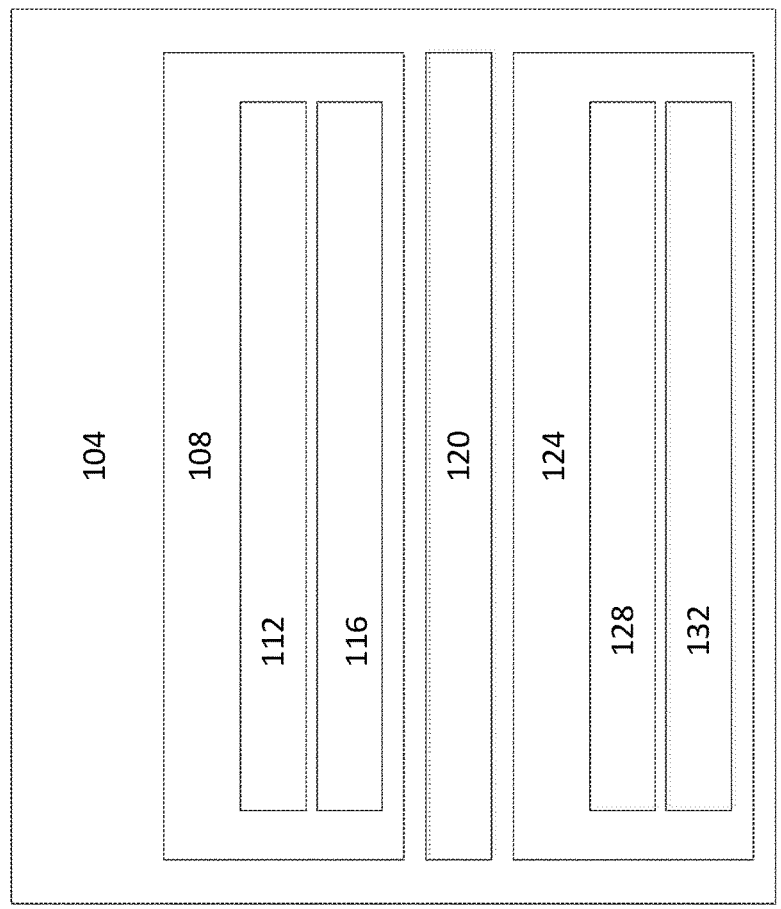
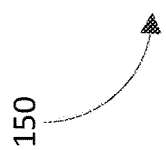
FIG. 1C

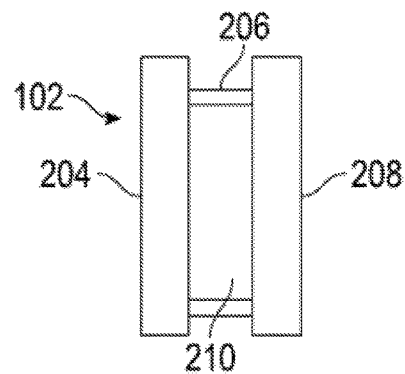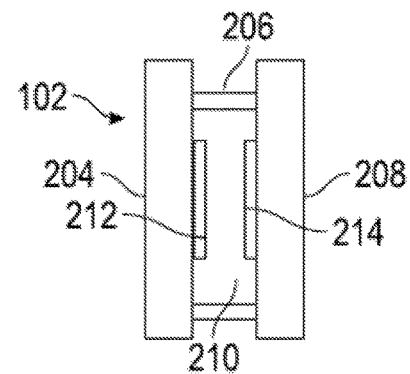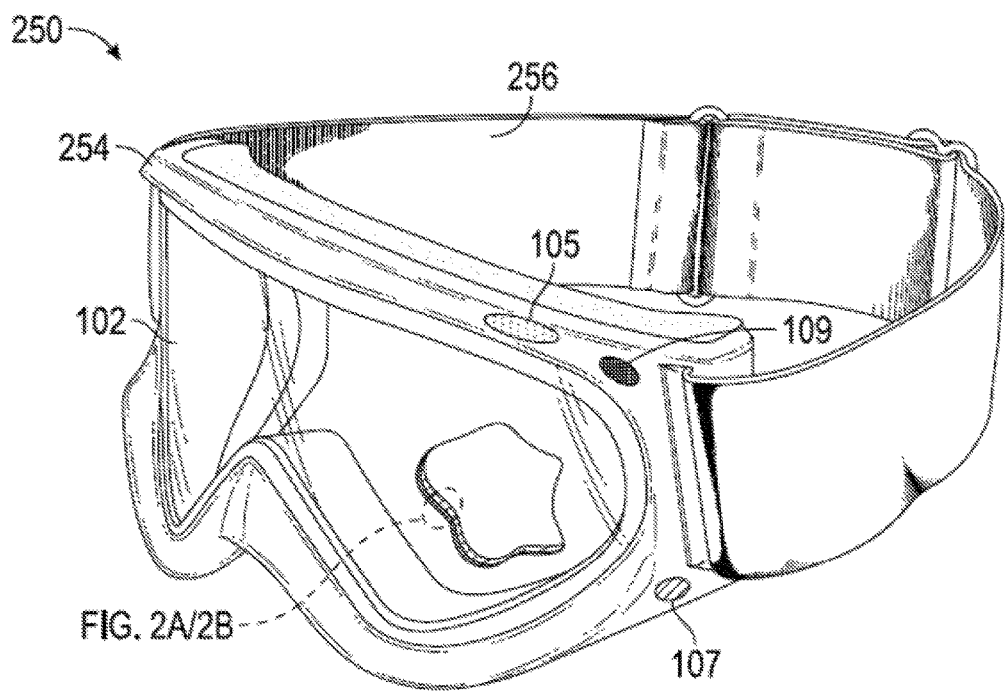

LAMINATED LENSES WITH ANTI-FOGGING FUNCTIONALITY

INCORPORATION BY REFERENCE OF RELATED APPLICATIONS

This application claims the benefit of priority under 35 USC §119 of U.S. Provisional Patent Application No. 62/377,478, filed on Aug. 19, 2016, titled "LAMINATED LENSES WITH ANTI-FOGGING FUNCTIONALITY." The entire contents of the above referenced application is incorporated by reference herein and made part of this specification.

PARTIES OF JOINT RESEARCH AGREEMENT

The subject matter disclosed in this application was developed and the claimed invention was made by, or on behalf of, Luxottica S.r.l. and Oakley, Inc., which are parties to a joint research agreement that was in effect on or before the effective filing date of the claimed invention. The claimed invention was made as a result of activities undertaken within the scope of the joint research agreement.

BACKGROUND

Field

This disclosure relates generally to eyewear and to lenses used in eyewear.

Description of Related Art

Eyewear can include one or more lenses attached to a frame configured to position the lenses on the wearer's head within the wearer's field of view. A lens for eyewear typically includes at least one lens layer made from a substantially rigid material, and a lens for eyewear can also include other layers of material, such as, for example, rigid or non-rigid materials that impart desired functionality or aesthetic characteristics to the lens. A lens element can include one lens layer or more than one lens layer, where each layer in the lens element is bonded together. A laminated lens can have two or more than two lens elements having respective mutually conforming surfaces which are adhered together. A laminated lens can be curved and have a variety of shapes.

SUMMARY

Example embodiments described herein have several features, no single one of which is indispensable or solely responsible for their desirable attributes. Without limiting the scope of the claims, some of the advantageous features will now be summarized.

Eyewear can include a laminated lens that has anti-fogging functionality. The lens can include an anti-fog layer configured to resist accumulation of condensate on a posterior surface of the lens and an interface layer comprising a thin layer of inorganic material with ceramic bulk properties. The interface layer can be disposed between the anti-fog layer and an adhesive layer configured to adhere to adjacent layers of the laminated lens. The adhesive layer can be disposed between two lens elements. One of the lens elements can include a polymer layer that provides stiffness to the lens and an electrically conductive layer deposited on the polymer layer. When electric current is applied across the electrically conductive layer via one or more electrodes, the lens can be heated.

A lens for eyewear can have a first lens element comprising an anti-fog layer configured to resist accumulation of condensate on a proximal surface of the first lens element; an interface layer comprising inorganic material with ceramic bulk properties; and an adhesive layer configured to adhere to adjacent layers of the lens. The interface layer can be disposed between the anti-fog layer and the adhesive layer.

In some embodiments, a lens has a second lens element comprising an electrically conductive layer configured to conduct electric current and a polymer layer configured to stiffen the lens. The adhesive layer can be disposed between the first lens element and the second lens element.

In certain embodiments, the anti-fog layer comprises cellulose acetate propionate. The cellulose acetate propionate can be activated such that it is hydrophilic. The anti-fog layer can have a thickness of 100 µm to 1000 µm. The interface layer can comprise chalcogenide glass, mineral oxide glass (such as, for example, amorphous silicon dioxide), or a chalcogenide or mineral oxide with microcrystalline structure. The interface layer can have a thickness of 1 nm to 100 nm or 5 nm to 20 nm. One or more electrodes can be in electrical communication with the electrically conductive layer.

Eyewear can include a proximal lens component and a distal lens component spaced apart from the proximal lens component, wherein the proximal lens component comprises the first lens element, the second lens element, and the adhesive layer. An insulating layer can be disposed between the proximal lens component and the distal lens component. The insulating layer can comprise air. The electrically conductive layer can comprise indium tin oxide. The polymer layer can comprise polyethylene terephthalate or polycarbonate. The adhesive layer can comprise optically clear adhesive having a luminous transmittance greater than or equal to 50% using CIE Illuminant D65. The adhesive layer can have a thickness of 10 µm to 300 µm. The adhesive layer can covalently bond to the first lens element and the second lens element.

A goggle can have a lens assembly comprising an anti-fog layer configured to resist accumulation of condensate on a proximal surface of the lens assembly while the goggle is worn; an interface layer comprising inorganic material with ceramic bulk properties; and an adhesive layer configured to adhere to adjacent layers of the lens assembly. The interface layer can be disposed between the anti-fog layer and the adhesive layer. The goggle can include a frame configured to support the lens assembly in a field of view of a wearer of the goggle. The frame can comprise a cushion component configured to substantially conform to at least a portion of a face of the wearer.

A goggle can have an anti-fog lens that attaches to a frame of the goggle, wherein the frame defines a central portion, wherein the frame comprises a bridge disposed at the central portion of the goggle frame, wherein the bridge comprises a nosepiece section, and wherein the frame comprises one or more recesses adapted to hold the lens within the field of view of the wearer.

In some embodiments, a helmet is attachable to a goggle with an anti-fog lens, wherein the frame of the goggle attaches to a base portion of the helmet. The base portion can be configured to absorb or distribute force from an impact. The base portion can comprise a shell and an inner layer coupled to the shell. The goggle can be releasably attachable to the base portion.

A method of manufacturing a lens for eyewear can include depositing an interface layer having a thickness of 1 nm to 100 nm or 5 nm to 20 nm onto an anti-fog layer configured to resist accumulation of condensate on a proximal surface of the lens while the eyewear is worn. The interface layer can comprise an inorganic material with ceramic bulk properties. A first lens element can comprise the interface layer and the anti-fog layer. The method can include disposing an adhesive layer on the first lens element. The adhesive layer can be configured to adhere to adjacent layers of the lens. The interface layer can be positioned between the anti-fog layer and the adhesive layer when the adhesive layer is disposed on the first lens element.

The method can further include depositing an electrically conductive layer configured to conduct electric current onto a polymer layer configured to stiffen the lens. A second lens element can comprise the polymer layer and the electrically conductive layer. The method can include connecting one or more electrodes to the electrically conductive layer and adhering, with the adhesive layer, the first lens element to the second lens element. A power supply can be connected to the one or more electrodes.

Depositing the interface layer can comprise a vapor deposition process. The vapor deposition process can comprise physical vapor deposition, an electron beam assisted physical vapor deposition process, a sputtering process, a chemical vapor deposition process, a plasma enhanced chemical vapor deposition process, a plasma enhanced physical vapor deposition process, an atomic layer deposition process, or a molecular beam epitaxy process.

Some embodiments provide a laminated anti-fog lens for eyewear having a first lens element comprising an anti-fog layer configured to resist accumulation of condensate on a proximal surface of the first lens element. The anti-fog layer can comprise a hydrophilic material such as, for example, cellulose acetate propionate. The anti-fog layer can be proximal to the wearer when the eyewear is worn. The anti-fog layer can have a thickness of 100 μm to 1000 μm. The lens can have an interface layer comprising glass, such as, for example, mineral oxide glass or chalcogenide glass. In addition or as an alternative, the interface layer can comprise inorganic material with microcrystalline structure. The interface layer can have a thickness of 1 nm to 100 nm or 5 nm to 20 nm. The lens can have a second lens element comprising an electrically conductive layer configured to conduct electric current when a power supply is electrically connected to the electrically conductive layer via one or more electrodes. The one or more electrodes can include a silver busbar. The electrically conductive layer can comprise a transparent conductor such as, for example, indium tin oxide. The lens can have a polymer layer configured to stiffen the lens. The polymer layer can comprise polyethylene terephthalate or polycarbonate. An adhesive layer can adhere to adjacent layers of the anti-fog lens. The interface layer can be positioned between the anti-fog layer and the adhesive layer. The adhesive layer can have a thickness of 10 μm to 300 μm. The adhesive layer can covalently bond to the adjacent layers.

An innovative aspect of the subject matter disclosed herein is embodied in a lens for eyewear comprising a first lens element and a second lens element. The first lens element comprises an anti-fog layer configured to resist accumulation of condensate on a proximal surface of the first lens element and an interface layer comprising an inorganic material with ceramic bulk properties. The interface layer is configured to facilitate the attachment of the anti-fog layer to adjacent layers of the lens. An adhesive layer may be disposed over the interface layer to facilitate attachment to adjacent layers of the lens. In some embodiments, an adhesive may be at least partially incorporated in the interface layer. In some embodiments, the interface layer may be configured to attach to adjacent layers of the lens without the use of an adhesive layer.

The second lens element comprises an electrically conductive layer configured to conduct electric current and a polymer layer configured to stiffen the lens. The first lens element can be adhered to the second lens element using an adhesive layer disposed between the first lens element and the second lens element.

The anti-fog layer can comprise cellulose acetate propionate. The anti-fog layer can have a thickness of 100 μm to 1000 μm. The interface layer can comprise chalcogenide glass or mineral oxide glass, such as, for example, silicon dioxide. The interface layer can be a nanoscale composite comprising the inorganic material present in a matrix of organic material. The interface layer can have a thickness of 1 nm to 100 nm, preferably 5 nm to 20 nm.

The lens can comprise one or more electrodes are in electrical communication with the electrically conductive layer. The lens can comprise a proximal lens component comprising the first lens element, the second lens element, and the adhesive layer. The lens can further comprise a distal lens component spaced apart from the proximal lens component. An insulating layer can be disposed between the proximal lens component and the distal lens component. The insulating layer can comprises air, a getter, a consuming air gap or combinations thereof. The electrically conductive layer can comprise indium tin oxide. The polymer layer can comprise polyethylene terephthalate, or polycarbonate. The adhesive layer can comprise optically clear adhesive having a luminous transmittance greater than or equal to 50% using CIE Illuminant D65. The adhesive layer can have a thickness of 10 μm to 300 μm. The adhesive layer can be configured to covalently bonds to the first lens element and the second lens element.

An innovative aspect of the subject matter disclosed herein is embodied in eyewear comprising a lens assembly. The lens assembly comprises an anti-fog layer configured to resist accumulation of condensate on a proximal surface of the lens assembly while the eyewear is worn. The lens assembly further comprises an interface layer comprising inorganic material with ceramic bulk properties. The lens assembly can further comprise an adhesive layer configured to adhere to adjacent layers of the lens assembly. The interface layer can be disposed between the anti-fog layer and the adhesive layer. The lens assembly can further comprise a frame configured to support the lens assembly in a field of view of a wearer of the eyewear.

The lens assembly can further comprise an electrically conductive layer configured to conduct electric current, wherein one or more electrodes are in electrical communication with the electrically conductive layer. The lens assembly can further comprise a polymer layer configured to stiffen the lens assembly. The anti-fog layer can comprise cellulose acetate propionate. The interface layer can have a thickness of 1 nm to 100 nm. The eyewear can be a goggle. When configured as a goggle, the frame can comprise a cushion component configured to substantially conform to at least a portion of a face of the wearer.

The various embodiments of lenses, lens elements, and/or lens assemblies discussed herein can be included in an eyewear comprising a frame. The eyewear discussed herein can be configured as a goggle comprising a head strap configured to secure the goggle to a head of a wearer, wherein the frame comprises a goggle frame having a central portion and comprising a bridge disposed at the central portion, the bridge comprising a nosepiece section, and wherein the goggle frame comprises one or more recesses adapted to hold the lens within a field of view of the wearer.

The eyewear discussed herein can be configured as a helmet, wherein the frame attaches to a base portion of the helmet, wherein the base portion is configured to absorb or distribute force from an impact, wherein the base portion comprises a shell and an inner layer coupled to the shell, and wherein the eyewear is releasably attachable to the base portion.

An innovative aspect of the subject matter disclosed herein is implemented in a lens for eyewear comprising an anti-fog layer configured to resist accumulation of condensate, wherein the anti-fog layer comprises a hydrophilic material; an interface layer comprising an inorganic material with ceramic bulk properties; and a lens component. The anti-fog layer can be proximal to the wearer when the eyewear is worn. The interface layer can be configured to facilitate attachment of the anti-fog layer to the lens component. The hydrophilic material can comprise cellulose acetate propionate. The interface layer can comprise silicon dioxide. The anti-fog layer can have a thickness between 100 μm to 1000 μm. The interface layer can have a thickness between 1 nm to 100 nm (e.g., between 5 nm and 20 nm).

The lens component can comprise a functional layer, wherein the functional layer comprises at least one of an electrically conductive layer, an electrochromic layer, a photochromic layer, a color filter, or a light attenuation filter. The functional layer can comprise an electrically conductive layer configured to conduct electric current when a power supply is electrically connected to the electrically conductive layer via one or more electrodes. The electrically conductive layer can comprise indium tin oxide. The one or more electrodes can comprise silver busbar. The electrically conductive layer can be disposed over a polymer layer configured to stiffen the lens. In some implementations, the functional layer can comprise an electrochromic layer.

The lens component can comprise an adhesive layer disposed over the interface layer such that the interface layer is between the adhesive layer and the anti-fog layer. The adhesive layer can have a luminous transmittance greater than or equal to 50% using CIE Illuminant D65. The lens component can comprise one or more spacers configured to provide a gap between the interface layer and lens component. The gap can comprise air, a gas (e.g., an inert gas or nitrogen) or a getter. The one or more spacers can comprise an adhesive. The adhesive layer can have a thickness between 10 μm and 300 μM.

The lens can comprise a proximal lens element and a distal lens element spaced apart from the proximal lens element. The proximal lens element can comprise the anti-fog layer, the interface layer, and the lens component. The lens can be included in an eyewear comprising a frame, wherein the lens is attached to the frame. The eyewear can be a goggle comprising a head strap configured to secure the goggle to a head of a wearer. In such embodiments, the frame can comprise a goggle frame. The goggle frame can comprise a central portion, and a bridge disposed at the central portion. The bridge can comprise a nosepiece section. The goggle frame can comprise one or more recesses adapted to hold the lens within a field of view of the wearer. The eyewear can be included in a helmet. The frame can be configured to attach to a base portion of the helmet. The base portion can be configured to absorb or distribute force from an impact. The eyewear can be releasably attachable to the base portion.

Another innovative aspect of the subject matter disclosed herein is implemented in a laminated anti-fog lens for eyewear comprising a first lens element, and a second lens element. The first lens element comprises an anti-fog layer configured to resist accumulation of condensate on a proximal surface of the first lens element. The anti-fog layer can comprise a hydrophilic material. The anti-fog layer can be proximal to the wearer when the eyewear is worn. The anti-fog layer can have a thickness between 100 μm and 1000 μm. The first lens element further comprises an interface layer having a thickness between 1 nm and 100 nm; and a functional layer. The interface layer can be disposed between the anti-fog layer and the functional layer. The functional layer can comprise an electrically conductive layer, the functional layer configured to conduct electric current when a power supply is electrically connected to the electrically conductive layer via one or more electrodes and generate joule heating when electric current flow therethrough. The functional layer can comprise at least one of an electrically conductive layer, an electrochromic layer, a photochromic layer, a color filter, or a light attenuation filter. The second lens element comprises a polymer layer, the second lens element spaced apart from the first lens element by a gap.

The hydrophilic material can comprise cellulose acetate propionate. The interface layer can comprise silicon dioxide. The lens can further comprise an adhesive layer between the interface layer and the functional layer, wherein the adhesive layer has a luminous transmittance greater than or equal to 50% using CIE Illuminant D65. The gap can comprise air, a gas (e.g., an inert gas), or a getter. The lens can further comprise a second functional layer. The second functional layer can comprise at least one of an electrically conductive layer, an electrochromic layer, a photochromic layer, a color filter, or a light attenuation filter.

Another innovative aspect of the subject matter disclosed herein is embodied in a lens for eyewear comprising a first lens element and an adhesive layer. The first lens element can comprise an anti-fog layer configured to resist accumulation of condensate and an interface layer comprising an inorganic material with ceramic bulk properties. The anti-fog layer can be disposed on a proximal surface of the first lens element. The interface layer is disposed between the anti-fog layer and the adhesive layer. The interface layer can facilitate the attached of the anti-fog layer to other layers of the lens. The interface layer can function as a moisture or vapor barrier and increase adhesion of the other layers of the lens to the anti-fog layer. The interface layer can reduce the risk of delamination of the various layers of the lens. The interface layer can provide a surface that enables covalent bonding to the adhesive layer to improve adhesion between the anti-fog layer and the other layers of the lens.

The lens can further comprise a second lens element. The adhesive layer can be disposed between the first lens element and the second lens element. The second lens element can comprise an electrically conductive layer configured to conduct electric current; and a polymer layer configured to stiffen the lens. The second lens element can comprise a functional layer, wherein the functional layer comprises at least one of an electrically conductive layer, an electrochromic layer, a photochromic layer, a color filter, or a light attenuation filter The anti-fog layer can comprise cellulose acetate propionate. The anti-fog layer can have a thickness of 100 μm to 1000 μm. The interface layer can have a thickness of 1 nm to 100 nm. The interface layer can comprise chalcogenide glass or mineral oxide glass. The interface layer can be a nanoscale composite comprising the inorganic material present in a matrix of organic material. The adhesive layer can comprise optically clear adhesive having a luminous transmittance greater than or equal to 50% using CIE Illuminant D65. The adhesive layer can have a thickness between 10 µm and 300 µm. The adhesive layer can covalently bond to the first lens element and the second lens element.

The lens can comprise a proximal lens component and a distal lens component spaced apart from the proximal lens component by an insulating layer. The insulating layer can comprise a gas. The proximal lens component can comprise the first lens element, the second lens element, and the adhesive layer.

Another innovative aspect of the subject matter disclosed herein is implemented in a method of manufacturing a lens for eyewear. The method comprises depositing an interface layer onto an anti-fog layer configured to resist accumulation of condensate. The anti-fog layer can be disposed on a proximal surface of the lens while the eyewear is worn. The method further comprises disposing a lens component over the interface layer, wherein the interface layer is configured to facilitate attachment of the anti-fog layer to the lens component. The anti-fog layer can comprise cellulose acetate propionate. The interface layer can comprise inorganic material with ceramic bulk properties.

The lens component can comprise a functional layer comprising an electrically conductive layer configured to conduct electric current. The method can further comprise depositing the electrically conductive layer onto a polymer layer configured to stiffen the lens; connecting one or more electrodes to the electrically conductive layer; and connecting a power supply to the one or more electrodes. Disposing the functional layer can comprises disposing an adhesive layer over the interface layer; and adhering, with the adhesive layer, the functional layer to the interface layer. Depositing the interface layer can comprise a vapor deposition process. The vapor deposition process can comprise at least one of an electron beam assisted physical vapor deposition process or a sputtering process.

BRIEF DESCRIPTION OF THE DRAWINGS

Various embodiments are depicted in the accompanying drawings for illustrative purposes, and should in no way be interpreted as limiting the scope of the inventions. In addition, various features of different disclosed embodiments can be combined to form additional embodiments, which are part of this disclosure. Any feature or structure can be removed or omitted. Throughout the drawings, reference numbers can be reused to indicate correspondence between reference elements.

FIG. 1A illustrates an example lens configuration having a lens element and an adhesive layer that can be included in the eyewear depicted in FIGS. 1D and 1n the goggles depicted in FIG. 2C.

FIGS. 1B and 1C illustrate example lens configurations having two lens elements joined by an adhesive layer that can be included in the eyewear depicted in FIGS. 1D and in the goggles depicted in FIG. 2C.

FIG. 2A illustrates an example lens configuration that can be included in the goggles depicted in FIG. 2C, the lens comprising a first component spaced apart from a second component by spacers.

FIG. 2B illustrates an example lens configuration that can be included in the goggles depicted in FIG. 2C, the lens comprising a first component spaced apart from a second component by a gap including one or more functional layers.

FIG. 2C illustrates an example goggle including an embodiment of a lens.

DETAILED DESCRIPTION OF CERTAIN EMBODIMENTS

Figure 1D:
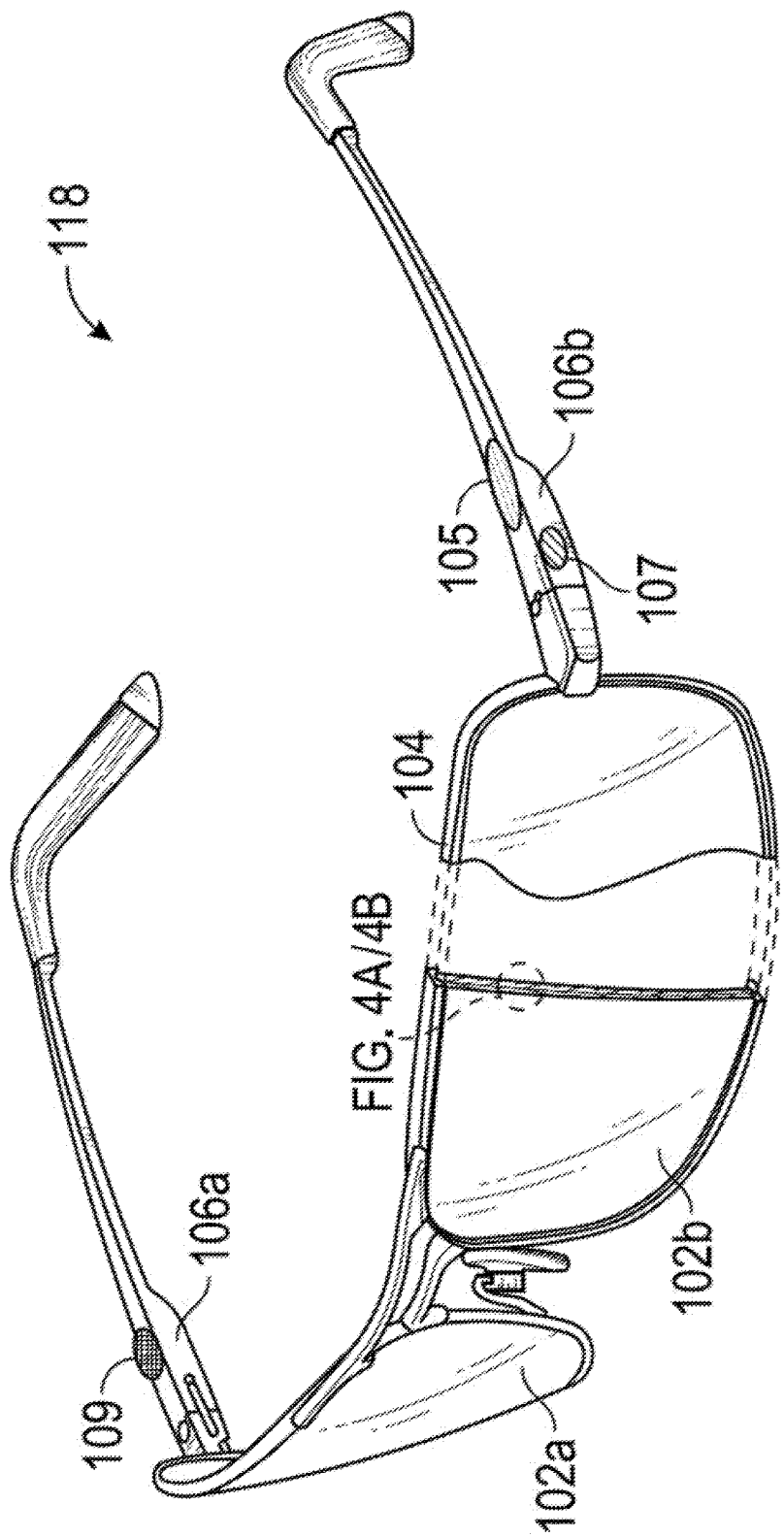
FIG. 1D illustrates an embodiment of eyewear including a pair of lenses.

Although certain embodiments and examples are disclosed herein, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Overview of Laminated Anti-Fog Eyewear

A lens for eyewear can include two or more than two lens elements bonded together to form a laminated lens. Each lens element can include one or more than one layer of material, wherein each layer is configured to impart specific functionality, performance characteristics, and/or aesthetic characteristics to the lens. Layers can be made from a variety of materials, including, for example, plastic materials, glass materials, microcrystalline materials, electrically conductive materials, thermally insulating materials, anti-fog materials, hydrophilic materials, hydrophobic materials, thin film materials, materials that can be injection molded, materials that can be extruded, materials that can be cast, materials that can be deposited by coating or vapor deposition processes, or a combination of materials. A laminated lens can be used in any type of eyewear, including, for example, spectacles, goggles, eyewear integrated into a helmet, general-purpose eyewear, special-purpose eyewear, sunglasses, driving glasses, sporting glasses, indoor eyewear, outdoor eyewear, vision-correcting eyewear, contrast-enhancing eyewear, eyewear designed for another purpose, or eyewear designed for a combination of purposes. The lens 102 can be corrective lenses or non-corrective lenses. The lens can be used in any wearable headwear with an optically transmissive element that could be configured to be placed in a user's line of sight. Example configurations of laminated lenses and methods of making laminated lenses are disclosed in International Patent Publication No. WO 2016/054198 and U.S. Patent Application Publication No. 2015/0131047, the entire contents of which are incorporated by reference herein and made a part of this specification.

In some embodiments, eyewear includes at least one lens configured for use in environments or activities that may lead to fogging of the lens. Such a lens can include one or more than feature designed to reduce fogging by, for example, resisting accumulation of condensate and/or removing accumulated condensate from a posterior and/or anterior surface of the lens. The posterior surface of a lens refers to the surface proximal to the eyes of a wearer of the lens when the eyewear is worn, while the anterior surface of the lens refers to the opposite surface, the surface distal to the eyes of the wearer of the lens when the eyewear is worn.

Environments or activities that may lead to fogging of goggles or other eyewear include, for example, skiing, motocross, underwater diving, and a variety of industrial safety applications, such as welding and use by power equipment operators. Typically, goggles and/or other types of eyewear offer some degree of visibility therethrough, while goggles also provide sealed protection to the eyes and adjacent areas of the wearer's face against particulate matter or water, without providing full head protection. Eyewear such as goggles can be worn in conjunction with, such as being attached to, a helmet that provides partial or full head protection. The helmet can be non-motorized.

One factor which affects vision through goggles and other eyewear in certain environments is fogging. Because the wearer's face is often warmer than the surrounding atmosphere for many applications (particularly for skiing, snowboarding, mountaineering, and other cold weather activities), the goggle lens is often colder than the air that is trapped between the wearer's face and the lens. Moisture in the trapped air (e.g., from the wearer's sweat) thus tends to condense upon the inside of a goggle lens. Indeed, in extremely cold conditions, as often encountered in snowsport applications, condensed moisture can even freeze upon the lens, clouding vision considerably.

One solution to this problem in the context of winter sport goggles is to vent moisture from the wearer's side of the goggle lenses to the outside of the lens. Vents along the peripheral wall of many goggles tend not to provide a sufficient air flow to materially reduce fogging. This lack of air flow can be corrected by using larger vents, but such a design risks allowing wind, snow, hard ice particles, etc. to enter the goggles, which would be counter to the purpose for the goggles. Another known art approach has been to include forward facing vents on the lens or lower frame. However, the air exchange rate then becomes a function of forward velocity. For example, high skiing speeds may produce too much ventilation (e.g., allowing more cold air into the goggle than is needed for fogging control, which can lead to discomfort to the wearer), while slow speeds or being stationary (e.g., standing in lift lines) will result in fogging. Thus, attempts to reduce fogging by providing ventilation have been limited and substantially unsuccessful.

Another solution to the problem of fogging in goggles is to provide insulation between the lens surface closest to the wearer's face and the cold outside atmosphere. Double lens structures, having spaced inner and outer lenses, provide such insulation in many goggle designs. Example double lens goggles are disclosed in U.S. Pat. Nos. 3,377,626; 3,591,864; and 4,571,748, the entire contents of which are incorporated by reference herein and made a part of this specification. However, although double lens structures may somewhat reduce fogging, such structures may not be sufficient to eliminate or sufficiently reduce fogging such that the wearer has an unobstructed view.

In certain embodiments, lens features designed to reduce fogging include an anti-fog layer. An anti-fog layer can provide an activated surface to absorb moisture from the air disposed between the posterior surface of the lens and the wearer. The surface can absorb moisture and also release the moisture under conditions that are both within the normal range of conditions encountered during a typical winter sport. In some embodiments, the antifogging surface is capable of dynamic saturation and water loss depending upon the surrounding environment, and is thus regeneratable under normal use conditions.

An example of an anti-fog layer that is regeneratable under normal use conditions is activated cellulose acetate. Example anti-fogging materials, example methods for activating materials to attain desired anti-fogging performance characteristics, and example anti-fog layers are disclosed in U.S. Patent Application Publication No. 2015/0374550, the entire contents of which are incorporated by reference herein and made a part of this specification.

An interface layer can be disposed on the anti-fog layer to facilitate attachment of the anti-fog layer to one or more lens components. The interface layer can be completely or partially in contact with the anti-fog layer and with one or more other lens components to promote attachment of the anti-fog layer to the one or more other lens components. The one or more lens components can comprise one or more adhesive layers, coatings, substrates, supports, spacers or combinations thereof. The one or more lens components can comprise one or more functional layers. A functional layer can comprise one or more layers, one or more coatings, one or more substrates, one or more laminates, or combinations thereof. The functional layer can include color enhancement filter, chroma enhancement filter, a laser attenuation filter, electrochromic cell, electrochromic filter, photoelectrochromic filter, variable attenuation filter, anti-reflection coating, interference stack, hard coating, flash mirror, anti-static coating, anti-fog coating, electrically conductive material, or combinations thereof. The functional layer can be configured to provide color enhancement functionality, light attenuation functionality, electrochromic functionality, photochromic functionality, heating functionality, electrical conduction functionality, anti-reflection functionality, anti-static functionality, anti-fog functionality, scratch resistance, mechanical durability, hydrophobic functionality, reflective functionality, darkening functionality, aesthetic functionality including tinting, or any combination of these. Examples of a functional layer providing one or more functionalities discussed herein are described in International Publication No. WO 2016/077431 and International Publication No. WO 2013/169987 both of which are incorporated by reference herein in their entirety for all that they disclose. Examples of color enhancement filters and/or chroma enhancement filters providing color enhancement, chroma enhancement and/or light attenuation functionalities are described in U.S. Pat. No. 8,770,749, U.S. Pat. No. 9,134,547 and U.S. Pat. No. 9,575,335 all of which are incorporated by reference herein in their entirety for all that they disclose.

Without subscribing to a particular theory, in some embodiments, the interface layer can facilitate attachment of the anti-fog layer to one or more lens components using a mechanism described herein, another mechanism that improves the attachment of the anti-fog layer to other lens components, or a combination of mechanisms. As an example, the interface layer can be completely or partially in contact with the anti-fog layer and to at least one of the one or more lens components. In various embodiments, the interface layer can be configured to function as a moisture or vapor barrier. For example, when the anti-fog layer is attached to other layers of the lens via an adhesive layer, the interface layer may create a moisture or vapor barrier between the anti-fog layer and the adhesive layer. Accordingly, the interface layer may increase adhesion between the anti-fog layer and other layers and/or lens components. In some embodiments, the interface layer may provide in-place stiffness to a substrate surface (such as, for example, a surface of the anti-fog layer). In some embodiments, the interface layer may provide a surface that enables covalent bonding of the interface layer to the adhesive layer.

In some embodiments, the interface layer facilitates attachment of the anti-fog layer to another lens component by resisting delamination of the anti-fog layer from the other lens component. In certain embodiments, the interface layer facilitates attachment of the anti-fog layer to other lens components by resisting delamination of lens components from each other. For example, a laminated lens with the interface layer can be less likely to delaminate as compared to a laminated lens that does not have the interface layer. Without subscribing to any particular theory, the laminated lens with the interface layer may be characterized by improved bonding of the layers to one another, improved delamination resistance when the lens is subjected to repeated temperature cycling, and/or improved delamination resistance when the lens is repeatedly exposed to moisture and/or other environmental stresses, compared to a laminated lens that does not have the interface layer. For example, a laminated lenses comprising an interface layer can exhibit optical quality transmission which does not delaminate after exposure to high humidity for extended periods of time and/or does not delaminate after repeated thermal cyclings over the temperature range of −40 to 80 degrees Celsius.

Various embodiments of the interface layer can comprise a thin, inorganic glass or microcrystalline layer. The interface layer can have reactive groups on its surface bonded to adjacent layers including but not limited to one of the following layers: a rigid organic plastic layer, an anti-fog layer, and an adhesive layer. Various embodiments of the interface layer can comprise a dielectric material. For example, the interface layer can comprise an inorganic material with ceramic bulk properties. The inorganic material can comprise a glass layer. The glass layer can be, for example, a mineral oxide glass (such as, for example, substantially stoichiometric silicon dioxide, silicon oxide, titanium oxide, etc.) and/or a chalcogenide glass.

The thickness of the interface layer can be selected to be greater than or equal to a minimum thickness to provide full coverage of a substrate and to be less than or equal to a maximum thickness to avoid cracking or crazing. The minimum and maximum thicknesses can depend on the type of material used. For example, the thickness of a silicon dioxide interface layer can be greater than or equal to 1 nm, greater than or equal to 2 nm, greater than or equal to 3 nm, greater than or equal to 5 nm, less than or equal to 20 nm, less than or equal to 50 nm, less than or equal to 100 nm, and/or between any two of the preceding thicknesses.

The interface layer material can be selected to achieve desired design goals of the lens. In some embodiments, ion beam assisted deposition (IBAD) and/or other deposition techniques can be used during deposition of at least a portion of the interface layer to select a desired hardness, crystalline microstructure, density, refractive index, and/or oxidation of the interface layer material. Examples of interface layer materials, methods of interface layer deposition, and interface layer configurations can be found in U.S. Patent Application Publication No. 2011/0229660, the entire contents of which are incorporated by reference herein and made a part of this specification. At least some of the inorganic interference coating materials or deposition techniques disclosed in the '660 application can be used as an interface layer material or deposition technique. The interface layer can include a layer of low-index material, a layer of high-index material, or a combination of low-index and high-index materials. In some embodiments, the materials and/or deposition techniques are selected to provide index matching to adjacent lens layers.

In some embodiments, at least a portion of the eyewear can be heated using a heating element. Heating of the eyewear can reduce fogging and improve visibility through the eyewear in certain environmental conditions. A lens can include a heating element that comprises an electrically conductive layer of material that is connectable to a power supply via one or more electrodes. In certain embodiments, the electrically conductive layer comprises indium oxide doped with tin oxide, zinc oxide doped with aluminum oxide, another suitable transparent conductive oxide, or a combination of materials. The thickness of the electrically conductive layer can be selected to achieve a desired resistance which, when attached to a power supply, generates a desired amount of joule heating when electric current flows therethrough.

A lens that includes both an anti-fog layer and an electrically conductive layer can include a bonding layer that adheres the anti-fog layer to a substrate with the electrically conductive layer disposed thereon. The bonding layer can comprise an optically clear adhesive and/or a pressure sensitive adhesive. In some embodiments an interface layer as described herein can be provided between the anti-fog layer and the electrically conductive layer.

Although some embodiments are discussed herein in terms of lenses having a lens body and/or optical-grade transparent sheet in a functional lens element comprising polyethylene terephthalate and/or polycarbonate, in some embodiments, the lens body and/or optical-grade transparent sheet can comprise any suitable optical grade lens material or combination of materials such as, for example and without limitation, polycarbonate (or PC), allyl diglycol carbonate monomer (being sold under the brand name CR-39®), glass, nylon, polyurethane, polyethylene, polyamide, polyethylene terephthalate (or PET), biaxially-oriented polyethylene terephthalate polyester film (or BoPET, with one such polyester film sold under the brand name MYLAR®), acrylic (polymethyl methacrylate or PMMA), a polymeric material, a co-polymer, or a doped material. Lenses described herein can have any suitable lens geometry, including, for example, spheroid, cylindrical, elliptical, toroidal, ovoid, or other aspheric shape in the horizontal and/or vertical planes. Examples of lens geometries are disclosed in U.S. Patent Application Publication No. 2015/0131047, the entire contents of which are incorporated by reference herein and made a part of this specification. Additionally, lenses of many front elevational shapes and orientations in the as-worn position can be used, beyond those illustrated herein.

Example Laminated Lens Configurations

FIG. 1A shows a schematic diagram of a lens configuration 100 for eyewear that includes an example lens 104 having a first lens element 108 and an adhesive layer 120 disposed adjacent to the lens element 108. The lens configuration 100 may be used in a variety of types of eyewear, such as, for example, the spectacles 118, the goggle 250, or the helmets 1300, 1400, 1600, as described herein. The first lens element 108 includes an anti-fog layer 112 and an interface layer 116 disposed such that the interface layer 116 is between the anti-fog layer 112 and the adhesive layer 120. In some embodiments, the interface layer 116 is adjacent to the anti-fog layer 112 and/or the adhesive layer 120, where adjacent means that the layers have touching surfaces and/or surfaces that are bonded to one another. As discussed herein, the interface layer 116 can advantageously improve adhesion of the anti-fog layer 112 to one or more adjacent layers. The interface layer 116 can resist delamination and remain in substantial contact with the anti-fog layer 112 and one or more adjacent layers thereby improving adhesion of the anti-fog layer 112 to one or more adjacent layers. The interface layer 116 may provide additional benefits as discussed herein. For example, the interface layer 116 may act as a moisture or vapor barrier and/or reduce the likelihood of delamination of the lens as a result of exposure to high humidity, repeated temperature cycling, and/or other environmental stresses over a period of time.

The interface layer 116 can comprise inorganic material with ceramic bulk properties. For example, the interface layer 116 can comprise a thin layer of glass, such as, for example, a chalcogenide glass or a mineral oxide glass such as amorphous silicon dioxide. In addition or as an alternative, the interface layer 116 can include inorganic material with microcrystalline structure. In certain embodiments, the interface layer 116 comprises substantially stoichiometric silicon dioxide and/or other stoichiometric material. The thickness of the interface layer 116 can be from 1 nm to 100 nm, from 5 nm to 20 nm, about 20 nm, or within another suitable range as discussed herein. The thickness of the interface layer 116 can be selected to permit the laminated lens 104 to be thermoformed without losing lens clarity and/or integrity. The thermoforming can be used to produce a curvature in the laminated lens 10. In some embodiments, a substantially flat lens may be thermoformed to create a curved lens. In certain embodiments, the laminated lens 104 is configured to be thermoformed without cracking or crazing of the interface layer 116.

In some embodiments, the anti-fog layer 112 is configured to resist accumulation of condensate on a proximal surface of the first lens element 108. The proximal surface of the first lens element 108 can be the posterior surface of the lens 104, such as, for example, the surface of the lens 104 closest to the eye of a wearer when the eyewear is worn. Alternatively, other lens layers or coatings can be between the eye of the wearer and the anti-fog layer 112. In some embodiments, the anti-fog layer 112 comprises a hydrophilic and/or water-permeable material, such as, for example, activated cellulose acetate propionate. The thickness of the anti-fog layer 112 can be from 100 μm to 1000 μm, from 300 μm to 800 μm, about 500 μm, or within another suitable range as discussed herein. The anti-fog layer 112 can reduce the humidity of air situated between the eyewear and the face of the wearer by absorbing moisture from the air.

In certain embodiments, the adhesive layer 120 is configured to adhere to adjacent layers of the lens. The adhesive layer 120 can comprise optically clear adhesive, such as, for example, an adhesive layer that has a luminous transmittance greater than or equal to 50%, greater than or equal to 75%, or greater than or equal to 90% using CIE Illuminant D65. The thickness of the adhesive layer 120 can be from 10 μm to 300 μm, from 30 μm to 100 μm, about 50 μm, or within another suitable range as discussed herein.

FIG. 1B illustrates a schematic diagram of a lens configuration 140 for eyewear comprising a first lens element 108 described with respect to FIG. 1A adhered to a second lens element 124 by the adhesive layer 120. The lens configuration 140 may be used in a variety of types of eyewear, such as, for example, the spectacles 118, the goggle 250, or the helmets 1300, 1400, 1600, as described herein. The second lens element 124 can comprise one or more functional layers. The one or more functional layers can comprise one or more layers, one or more coatings, one or more substrates, one or more laminates, or combinations thereof. The one or more functional layers can be provided by disposing one or more layers, coatings or laminates on a substrate. Examples of functional layers can include color enhancement filters, chroma enhancement filters, a laser attenuation filter, electrochromic filters, photoelectrochromic filters, variable attenuation filters, anti-reflection coatings, interference stacks, hard coatings, flash mirrors, anti-static coatings, anti-fog coatings, electrically conductive materials, or combinations thereof. The one or more functional layers of the second lens element 124 can be configured to provide color enhancement functionality, light attenuation functionality, electrochromic functionality, photochromic functionality, heating functionality, electrical conduction functionality, anti-reflection functionality, anti-static functionality, anti-fog functionality, scratch resistance, mechanical durability, hydrophobic functionality, reflective functionality, darkening functionality, aesthetic functionality including tinting, or any combination of these. Examples of one or more functional layers providing one or more functionalities are described in International Publication No. WO 2016/077431 and International Publication No. WO 2013/169987 both of which are incorporated by reference herein in their entirety for all that they disclose. Examples of color enhancement filters and/or chroma enhancement filters providing color enhancement, chroma enhancement and/or light attenuation functionalities are described in U.S. Pat. No. 8,770,749, U.S. Pat. No. 9,134,547 and U.S. Pat. No. 9,575,335 all of which are incorporated by reference herein in their entirety for all that they disclose.

With continued reference to lens 140, the first lens element 108 can include one or more interface layers, vapor barrier layers, one or more electrically conductive layers, one or more electrochromic layers, one or more acetate layers, one or more oxide layers, one or more adhesive layers, one or more air gaps, one or more optical filters, or combinations thereof in addition to the anti-fog layer 112 and the interface layer 116. The second lens element 124 can comprise one or more interface layers, vapor barrier layers, one or more electrically conductive layers, one or more electrochromic layers, one or more acetate layers, one or more oxide layers, one or more adhesive layers, one or more air gaps, or combinations thereof as described herein.

FIG. 1C shows a schematic diagram of an example lens configuration 150 for eyewear in which the first lens element 108 described with respect to FIG. 1A is joined to a second lens element 124 described with respect to FIG. 1B by the adhesive layer 120. The lens configuration 150 may be used in a variety of types of eyewear, such as, for example, the spectacles 118, the goggle 250, or the helmets 1300, 1400, 1600, as described herein. The second lens element 124 includes an electrically conductive layer 128 and a polymer layer 132 disposed such that the electrically conductive layer 128 is between the adhesive layer 120 and the polymer layer 132. In some embodiments, the electrically conductive layer 128 is adjacent to the adhesive layer 120 and/or the polymer layer 132. In various embodiments, the polymer layer 132 can comprise a substrate to support the electrically conductive layer 128 and/or one or more additional functional layers. Although, in the illustrated configuration, the electrically conductive layer 128 is between the adhesive layer 120 and the polymer layer 132, in other configurations, the polymer layer 132 can be between the adhesive layer 120 and the electrically conductive layer 128.

The lens 150 can further comprise one or more layers including but not limited to an interface layer, an adhesive layer, an air gap, a color filter, an interference filter, a chroma enhancement filter, an electrochromic layer, a photochromic layer, a dielectric layer, an oxide layer, an acetate layer, transparent conducting oxides, metal layers, or combinations thereof can be disposed between the polymer layer 132 and the electrically conductive layer 128. In various embodiments of the lens 150, an interface layer, an adhesive layer, an air gap, a color filter, an interference filter, a chroma enhancement filter, an electrochromic layer, a photochromic layer, a dielectric layer, an oxide layer, an acetate layer, transparent conducting oxides, metal layers, or combinations thereof can be disposed on a side of the polymer layer 132 opposite the side facing the electrically conductive layer 128. In some embodiments of the lens 150, an interface layer, an adhesive layer, an air gap, a color filter, an interference filter, a chroma enhancement filter, an electrochromic layer, a photochromic layer, a dielectric layer, an oxide layer, an acetate layer, transparent conducting oxides, metal layers, or combinations thereof can be disposed on a side of the electrically conductive layer 128 opposite the side facing the polymer layer 132.

With continued reference to lens 140, the first lens element 108 can include an interface layer, an adhesive layer, an air gap, a color filter, an interference filter, a chroma enhancement filter, an electrochromic layer, a photochromic layer, a dielectric layer, an oxide layer, an acetate layer, transparent conducting oxides, metal layers, or combinations thereof in addition to the anti-fog layer 112 and the interface layer 116.

In some embodiments, the electrically conductive layer 128 is configured to conduct electric current when a power supply is electrically connected to the electrically conductive layer 128 via one or more electrodes. The one or more electrodes can comprise a metal electrode, a busbar, a copper busbar, and/or a silver busbar. In some embodiments, the busbar has a thickness of 10 µm to 30 µm, about 15 µm, or another suitable thickness. The electrically conductive layer 128 can be made from a transparent conductor, such as, for example, indium tin oxide (ITO), graphene, ITO silver, and/or another electrically conductive material as disclosed herein. The thickness of the electrically conductive layer 128 can be selected to provide a desired amount of joule heating when electric current is provided across the electrically conductive layer 128. For example, the thickness of the electrically conductive layer 128 can be 10 µm to 100 µm, about 30 µm, or another suitable thickness. The thickness of the electrically conductive layer 128 can be reduced (for example, reduced by the thickness of the one or more electrodes) in any areas of the lens where the electrically conductive layer 128 is stacked with the one or more electrodes (see, e.g., FIGS. 4A and 4B). In some embodiments, the electrically conductive layer 128 is in a 180-degree orientation.

In certain embodiments, the polymer layer 132 is configured to stiffen the lens 104. The polymer layer 132 can comprise polyethylene terephthalate (PET), polycarbonate (PC), another polymer material as disclosed herein, and/or a co-polymer. The thickness of the polymer layer 132 can be selected such that the lens 104 has a desired overall thickness, such as, for example, a thickness of 0.5 mm to 3.5 mm, 0.8 mm to 2.6 mm, about 1.5 mm, or another suitable thickness.

Example Goggle Configurations

FIG. 1D illustrates an embodiment of eyewear 118 that can incorporate various lenses and/or lens configurations disclosed herein. The eyewear 118 can include a pair of lenses 102a, 102b. The eyewear can be of any type, including general-purpose eyewear, special-purpose eyewear, sunglasses, driving glasses, sporting glasses, goggles, indoor eyewear, outdoor eyewear, vision-correcting eyewear, contrast-enhancing eyewear, eyewear designed for another purpose, or eyewear designed for a combination of purposes. The lenses 102a and 102b can be corrective lenses or non-corrective lenses and can be made of any of a variety of optical materials including glass and/or plastics, such as, for example, acrylics or polycarbonates, as described in more detail below. The lenses can have various shapes. For example, the lenses 102a, 102b can be flat, have 1 axis of curvature, 2 axes of curvature, or more than 2 axes of curvature, the lenses 102a, 102b can be cylindrical, parabolic, spherical, flat, or elliptical, or any other shape such as a meniscus or catenoid. When worn, the lenses 102a, 102b can extend across the wearer's normal straight ahead line of sight, and can extend substantially across the wearer's peripheral zones of vision. As used herein, the wearer's normal line of sight shall refer to a line projecting straight ahead of the wearer's eye, with substantially no angular deviation in either the vertical or horizontal planes. In some embodiments, the lenses 102a, 102b extend across a portion of the wearer's normal straight ahead line of sight.

The outside surface of lenses 102a or 102b can conform to a shape having a smooth, continuous surface having a constant horizontal radius (sphere or cylinder) or progressive curve (ellipse, toroid or ovoid) or other aspheric shape in either the horizontal or vertical planes. The geometric shape of other embodiments can be generally cylindrical, having curvature in one axis and no curvature in a second axis. The lenses 102a, 102b can have a curvature in one or more dimensions. For example, the lenses 102a, 102b can be curved along a horizontal axis. As another example, lenses 102a, 102b can be characterized in a horizontal plane by a generally arcuate shape, extending from a medial edge throughout at least a portion of the wearer's range of vision to a lateral edge. In some embodiments, the lenses 102a, 102b are substantially linear (not curved) along a vertical axis. In some embodiments, the lenses 102a, 102b have a first radius of curvature in one region, a second radius of curvature in a second region, and transition sites disposed on either side of the first and second regions. The transition sites can be a coincidence point along the lenses 102a, 102b where the radius of curvature of the lenses 102a, 102b transitions from the first to the second radius of curvature, and vice versa. In some embodiments, lenses 102a, 102b can have a third radius of curvature in a parallel direction, a perpendicular direction, or some other direction. In some embodiments, the lenses 102a, 102b can lie on a common circle. The right and left lenses in a high-wrap eyeglass can be canted such that the medial edge of each lens will fall outside of the common circle and the lateral edges will fall inside of the common circle. Providing curvature in the lenses 102a, 102b can result in various advantageous optical qualities for the wearer, including reducing the prismatic shift of light rays passing through the lenses 102a, 102b, and providing an optical correction.

A variety of lens configurations in both horizontal and vertical planes are possible. Thus, for example, either the outer or the inner or both surfaces of the lens 102a or 102b of some embodiments can generally conform to a spherical shape or to a right circular cylinder. Alternatively either the outer or the inner or both surfaces of the lens may conform to a frusto-conical shape, a toroid, an elliptic cylinder, an ellipsoid, an ellipsoid of revolution, other asphere or any of a number of other three dimensional shapes. Regardless of the particular vertical or horizontal curvature of one surface, however, the other surface may be chosen such as to minimize one or more of power, prism, and astigmatism of the lens in the mounted and as-worn orientation.

The lenses 102a, 102b can be linear (not curved) along a vertical plane (e.g., cylindrical or frusto-conical lens geometry). In some embodiments, the lenses 102a, 102b can be aligned substantially parallel with the vertical axis such that the line of sight is substantially normal to the anterior surface and the posterior surface of the lenses 102a, 102b. In some embodiments, the lenses 102a, 102b are angled downward such that a line normal to the lens is offset from the straight ahead normal line of sight by an angle $\phi$. The angle $\phi$ of offset can be greater than about 0° and/or less than about 30°, or greater than about 70° and/or less than about 20°, or about 15°, although other angles $\phi$ outside of these ranges may also be used. Various cylindrically shaped lenses may be used. The anterior surface and/or the posterior surface of the lenses 102a, 102b can conform to the surface of a right circular cylinder such that the radius of curvature along the horizontal axis is substantially uniform. An elliptical cylinder can be used to provide lenses that have non-uniform curvature in the horizontal direction. For example, a lens may be more curved near its lateral edge than its medial edge. In some embodiments, an oblique (non-right) cylinder can be used, for example, to provide a lens that is angled in the vertical direction.

In some embodiments, the eyewear 118 incorporates canted lenses 102a, 102b mounted in a position rotated laterally relative to conventional centrally oriented dual lens mountings. A canted lens may be conceived as having an orientation, relative to the wearer's head, which would be achieved by starting with conventional dual lens eyewear having centrally oriented lenses and bending the frame inwardly at the temples to wrap around the side of the head. When the eyewear 118 is worn, a lateral edge of the lens wraps significantly around and comes in close proximity to the wearer's temple to provide significant lateral eye coverage.

A degree of wrap may be desirable for aesthetic styling reasons, for lateral protection of the eyes from flying debris, or for interception of peripheral light. Wrap may be attained by utilizing lenses of tight horizontal curvature (high base), such as cylindrical or spherical lenses, and/or by mounting each lens in a position which is canted laterally and rearwardly relative to centrally oriented dual lenses. Similarly, a high degree of rake or vertical tilting may be desirable for aesthetic reasons and for intercepting light, wind, dust or other debris from below the wearer's eyes. In general, "rake" will be understood to describe the condition of a lens, in the as-worn orientation, for which the normal line of sight strikes a vertical tangent to the lens 102a or 102b at a non-perpendicular angle.

The lenses 102a, 102b can be provided with anterior and posterior surfaces and a thickness therebetween, which can be variable along the horizontal direction, vertical direction, or combination of directions. In some embodiments, the lenses 102a, 102b can have a varying thickness along the horizontal or vertical axis, or along some other direction. In some embodiments, the thickness of the lenses 102a, 102b tapers smoothly, though not necessarily linearly, from a maximum thickness proximate a medial edge to a relatively lesser thickness at a lateral edge. The lenses 102a, 102b can have a tapering thickness along the horizontal axis and can be decentered for optical correction. In some embodiments, the lenses 102a, 102b can have a thickness configured to provide an optical correction. For example, the thickness of the lenses 102a, 102b can taper from a thickest point at a central point of the lenses 102a, 102b approaching lateral segments of the lenses 102a, 102b. In some embodiments, the average thickness of the lenses 102a, 102b in the lateral segments can be less than the average thickness of the lenses 102a, 102b in the central zone. In some embodiments, the thickness of the lenses 102a, 102b in at least one point in the central zone can be greater than the thickness of the lenses 102a, 102b at any point within at least one of the lateral segments.

In some embodiments, the lenses 102a, 102b can be finished, as opposed to semi-finished, with the lenses 102a, 102b being contoured to modify the focal power. In some embodiments, the lenses 102a, 102b can be semi-finished so that the lenses 102a, 102b can be capable of being machined, at some time following manufacture, to modify their focal power. In some embodiments, the lenses 102a, 102b can have optical power and can be prescription lenses configured to correct for near-sighted or far-sighted vision. The lenses 102a, 102b can have cylindrical characteristics to correct for astigmatism.

The eyewear 118 can include a mounting frame 104 configured to support the lenses 102a, 102b. The mounting frame 104 can include orbitals that partially or completely surround the lenses 102a, 102b. Referring to FIG. 1D, it should be noted that the particular mounting frame 104 is not essential to the embodiment disclosed herein. The frame 104 can be of varying configurations and designs, and the illustrated embodiment shown in FIG. 1D is provided as examples only. As illustrated, the frame 104 may include a top frame portion and a pair of ear stems 106a, 106b that are connected to opposing ends of the top frame portion. Further, the lenses 102a, 102b may be mounted to the frame 104 with an upper edge of the lens 102a or 102b extending along or within a lens groove and being secured to the frame 104. For example, the upper edge of the lens 102a or 102b can be formed in a pattern, such as a jagged or non-linear edge, and apertures or other shapes around which the frame 104 can be injection molded or fastened in order to secure the lens 102a or 102b to the frame 104. Further, the lenses 102a, 102b can be removably attachable to the frame 104 by means of a slot with inter-fitting projections or other attachment structure formed in the lenses 102a, 102b and/or the frame 104.

It is also contemplated that the lenses 102a, 102b can be secured along a lower edge of the frame 104. Various other configurations can also be utilized. Such configurations can include the direct attachment of the ear stems 106a, 106b to the lenses 102a, 102b without any frame, or other configurations that can reduce the overall weight, size, or profile of the eyeglasses. In addition, various materials can be utilized in the manufacture of the frame 104, such as metals, composites, or relatively rigid, molded thermoplastic materials which are well known in the art, and which can be transparent or available in a variety of colors. Indeed, the mounting frame 104 can be fabricated according to various configurations and designs as desired. In some embodiments, the frame 104 is configured to retain a unitary lens that is placed in front of both eyes when the eyewear is worn. Eyewear (e.g., goggles) can also be provided that include a unitary lens that is placed in front of both eyes when the eyewear is worn.

In some embodiments, the ear stems 106a, 106b can be pivotably attached to the frame 104. In some embodiments, the ear stems 106a, 106b attach directly to the lenses 102a, 102b. The ear stems 106a, 106b can be configured to support the eyewear 118 when worn by a user. For example, the ear stems 106a, 106b can be configured to rest on the ears of the user. In some embodiments, the eyewear 118 includes a flexible band used to secure the eyewear 118 in front of the user's eyes in place of ear stems 106a, 106b.

Some embodiments provide for eyewear 118 having electrically-powered functionality (such as, for example, a heating element) incorporated into the lenses 102a, 102b, into the frame 104, and/or into other components of the eyewear 118. The eyewear 118 can include a power source 105, such as a battery, an electrical contact, and a conductor that conveys a voltage to an electrode in the lenses 102a, 102b. In some embodiments, the eyewear 118 includes control logic connected to one or more sensors for automatic adjustment of an electrically-powered component of the eyewear. The one or more sensors can comprise temperature sensors, humidity sensors, and/or some other type of sensor that can detect a change in the environment and automatically control the electrically-powered component. The eyewear 118 can include a user interface element 107 integrated into the frame 104, the ear stems 106a, 106b, the lens 102a, 102b, or any combination of these. The user interface element 107 can be configured to allow the user to control activation and deactivation of the electrically-powered component. The user interface element 107 can be a switch, button, toggle, slide, touch-interface element, knob, other mechanical feature, or other electrical feature. For example, the user interface element 107 can include a touch-sensitive region where if a user contacts said region the electrically-powered component changes state. The eyewear 118 can include a sensor 109 integrated into the frame 104, the ear stems 106a, 106b, the lens 102a, 102b, or any combination of these. The sensor 109 can include a control circuit that can provide a signal to activate and deactivate the electrically-powered component in response to a change in the environment.

FIG. 2A illustrates an embodiment of lens configuration 102 including multiple lens components 204, 208 that are spaced apart. The lens configuration 102 can be included in goggles or other eyewear. The lens 102 includes a first component 204 spaced apart from a second component 208 by spacers 206. A gap 210 is included between the first component 204 and the second component 208.

The first component 204 can include a polymer lens body, such as, for example, one of the polymer layers described herein. In some embodiments, the first component 204 can comprise a substrate layer including polycarbonate (PC), nylon, polyurethane, polyethylene, polyethylene terephthalate (PET), polyimide, acrylic, MYLAR®, clear glass, doped glass, or filtered glass. The thickness of the first component 204 can be between about 0.02 inches and about 0.1 inches. The first component 204 has an inner surface facing the second component 208 and an outer surface opposite the inner surface. The inner and outer surfaces of the first component 204 can be planar or curved. The inner and/or outer surfaces of the first component 204 can be tinted. In some embodiments, the inner and/or outer surfaces of the first component 204 can be clear. In various embodiments, the outer surface of the first component 204 can be configured to receive ambient incident light.

Figure 4A:
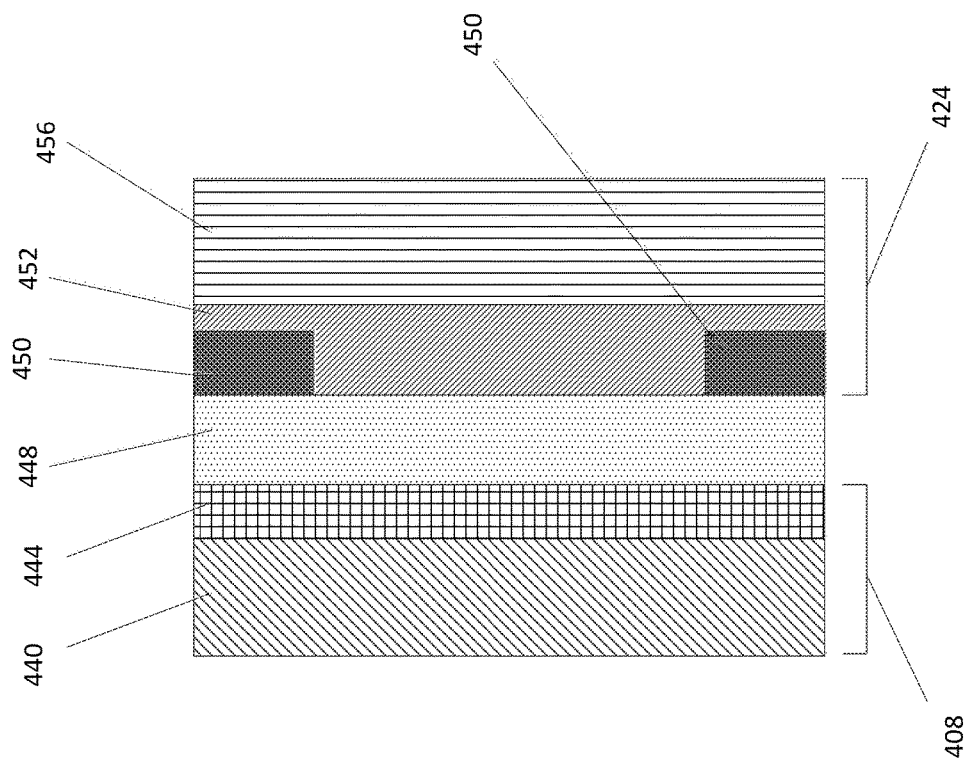
FIG. 4A illustrates an example lens configuration of a laminated lens that resists accumulation of condensate thereon.

The second component 208 can be an anti-fog lens, such as, for example, one of the lenses with anti-fog functionality disclosed herein (including those shown by way of example and not limitation in FIGS. 1A, 1C, and 4A). The anti-fog lens can include a substrate to which an anti-fog layer is applied. The thickness of the second component 208 can be between about 0.02 inches and about 0.1 inches. The second component 208 can be tinted. The second component 208 has a first surface facing the first component 204 and a second surface opposite the first surface. The first and second surfaces of the second component 208 can be planar or concave in one or more dimensions. In various embodiments, incident ambient light can be transmitted out of the lens towards the eye through the second surface The spacers 206 can comprise foam or any other suitable material such as, for example, metal, polymer, PC, nylon, polyurethane, polyethylene, polyimide, PET, acrylic, or MYLAR®. In various embodiments, the spacers 206 can include discrete structures that are disposed between the first component 204 and second component 208. In some embodiments, the spacers 206 can be part of a unitary structure (e.g., a ring or a semicircular shaped structure). The spacers 206 can be attached to the first component 204 and the second component 208 by adhesives such as, for example, thermal or UV cured adhesive or Pressure Sensitive Adhesive (PSA). In some embodiments, spacers 206 can be attached to the first component 204 and the second component 208 by electrostatic adhesion. In some embodiments, spacers 206 can be attached to the first component 204 and the second component 208 mechanically.

The gap 210 between the first component 204 and the second component 208 can include air and/or other gasses. In some embodiments, the gap 210 can include a suitable material that provides thermal insulation. The gap 210 can have a thickness between about 0.001 inches and about 0.25 inches. In some embodiments, the gap 210 has a thickness greater than or equal to 0.05 inches and/or less than or equal to 0.25 inches. Although, the illustrated implementation includes a gap 210, other implementations of the gap 210 may be configured without the gap 210. In some embodiments, the gap 210 between the first component 204 and the second component 208 can include one or more functional layers 212 and 214 as shown in FIG. 2B. The one or more functional layers 212 and 214 can include an interference stack, flash mirror, photochromic layer(s), anti-reflective coating, anti-static layer, liquid containing layer(s), electrochromic layer(s), chroma enhancement layer, color enhancement layer, contrast enhancement layer, trichoic filter, glass layer, and/or hybrid glass-plastic layer. The one or more functional layers can also be applied to one of the surfaces of the first component 204 and/or the second component 208. As described above, a functional layer can comprise one or more layers, one or more coatings, one or more substrates, one or more laminates, or combinations thereof.

As noted above, the second component 208 can be an anti-fog lens element. In some embodiments, the second component 208 can comprise an anti-fog layer and an interface layer that facilitates attachment of the anti-fog layer to the functional layer 214. The functional layer 214 can comprise a polymer substrate and an electrically conductive layer. The second component 208 and/or the functional layer 214 can further comprise one or more additional layers including but not limited to an interface layer, an adhesive layer, an air gap, a color filter, an interference filter, a chroma enhancement filter, an electrochromic layer, a photochromic layer, a dielectric layer, an oxide layer, an acetate layer, transparent conducting oxides, metal layers, or combinations thereof.

In various embodiments, the first component 204 and/or the second component 208 can include a violet edge filter that absorbs wavelength less than 390 nm and transmits wavelengths between 390 nm and 800 nm. In various embodiments, the first component 204 and/or the second component 208 can also include an UV light absorbing filter.

FIG. 2C illustrates a perspective view of an embodiment of a goggle 250 including an embodiment of a lens 102. The goggle 250 can be configured as a ski google, a snow goggle, a motocross goggle, or any other type of goggle. The lens 102 can extend in the path of a wearer's left and right eye fields of vision. In various embodiments, the curvature of the lens 102 can allow it to conform closely from side to side to the wearer's face, thus maximizing the interception of sun and other strong light sources, while at the same time providing comfort and pleasing aesthetic characteristics.

The lens 102 can be of a single pane of material. Thus, the lens 102 can be unitary or have a dual lens design. A nosepiece opening can be formed along the lower edge of a frame 254, which can be sized and configured to accommodate the nose of a wearer. Furthermore, the lower edge of the frame 254 can also be shaped to substantially conform to the wearer's facial profile, thus allowing some embodiments to be closely fitted to the wearer's head while not contacting the skin of the wearer's face and other embodiments to contact the wearer's face at multiple points to create an enclosure. The goggles 250 can include a strap 256 that can be configured to substantially secure the goggles 250 in a fixed location relative to the wearer's face and/or create an effective seal against the wearer's face to impede or prevent the entrance of water, snow, dirt, or other particulates into the enclosed area.

One, any combination of more than one, or all of the features described with reference to the eyewear 118 can likewise be embodied in the goggles 250 disclosed herein. For example, the goggles 250 can include the power source 105, such as a battery, the electrical contact, and the conductor that conveys a voltage to the lens 102, the control logic connected to one or more sensors for automatic adjustment of any powered components, such as, for example, lens heating functionality and/or a variable filter component of the lens 102, the user interface element 107, and/or the sensor 109 including a control circuit that can provide a signal to control the powered components of the lens 102.

Example Helmets with Anti-Fogging Eyewear

Some embodiments provide a helmet that can be used with anti-fogging eyewear. For example, the helmet can have an adjustable adapter module for use with goggles (for example, for use with goggles with or without a head strap), such as, for example, embodiments of helmets described with reference to FIG. 3A-3C, or can have eyewear integrated into a helmet face shield. In some embodiments, the eyewear is integral with a helmet. In other embodiments, the helmet includes an eyewear adapter module configured to attach the eyewear to the helmet. Examples of helmets that can be used with anti-fogging eyewear are disclosed in International Patent Application No. PCT/US2016/038250, the entire contents of which are incorporated by reference herein and made a part of this specification.

Figure 3A:
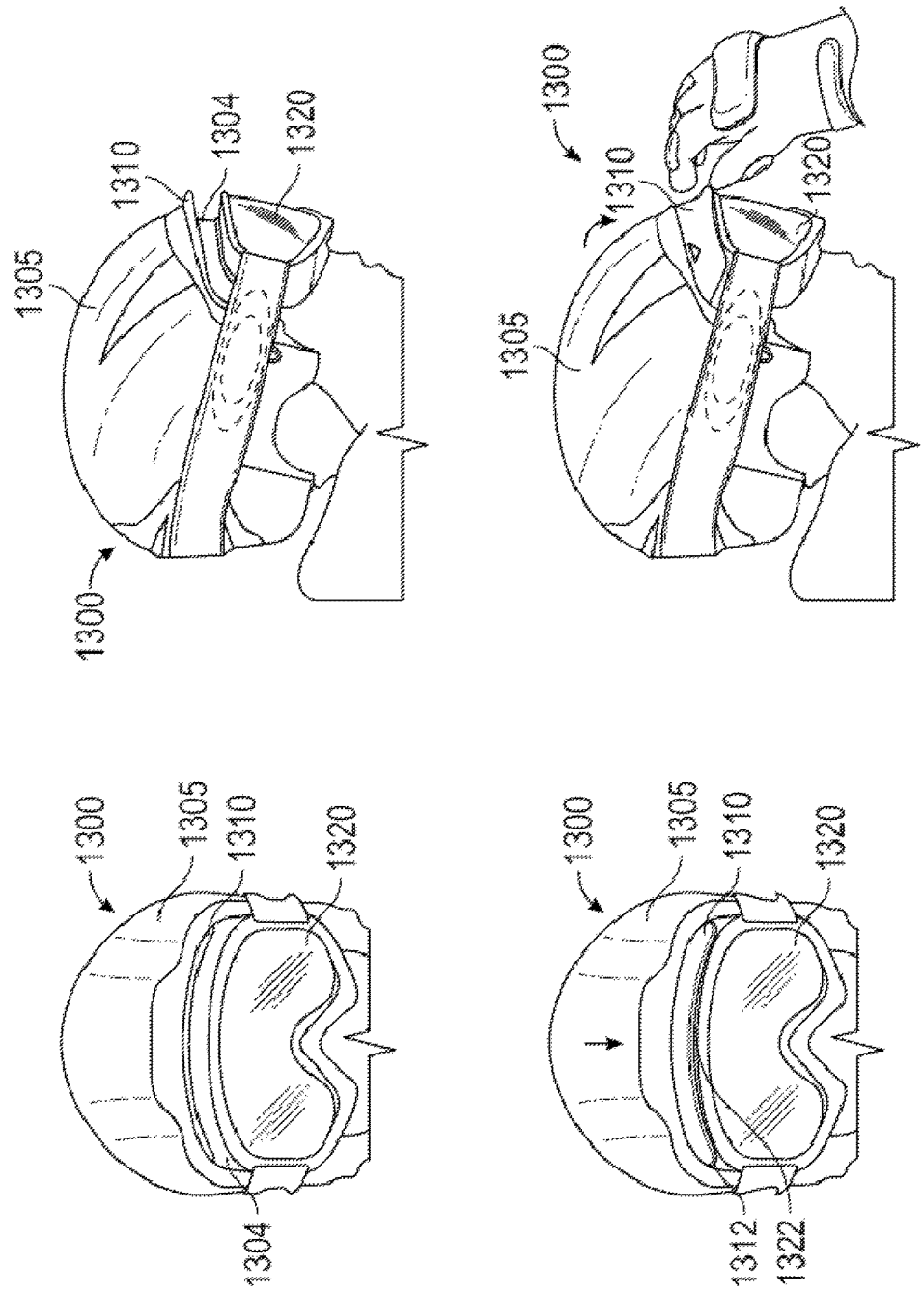
FIG. 3A illustrates an example helmet having eyewear including an embodiment of a lens.
Figure 3B:
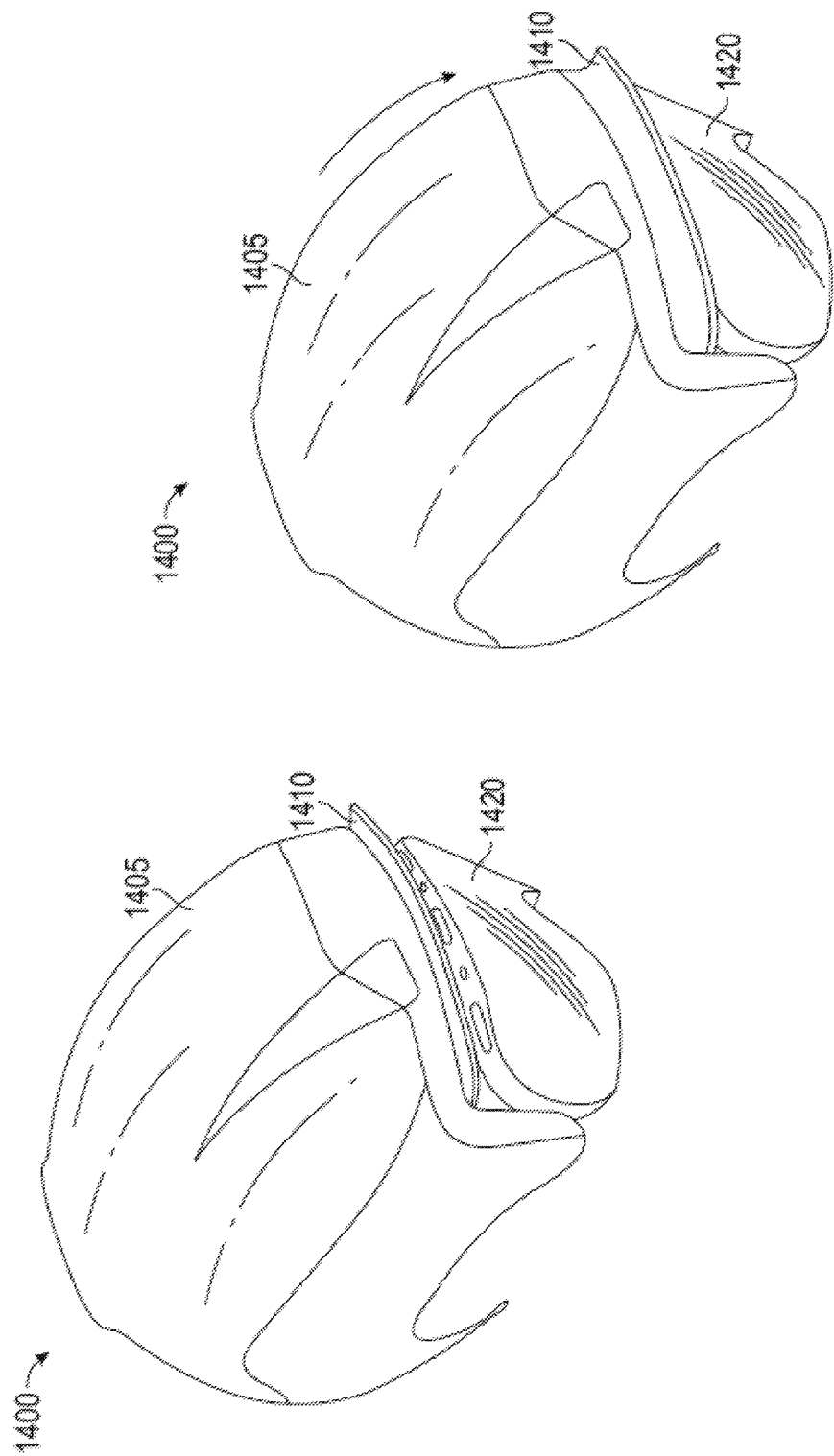
FIG. 3B illustrates another example of a helmet having eyewear including an embodiment of a lens.
Figure 3C:
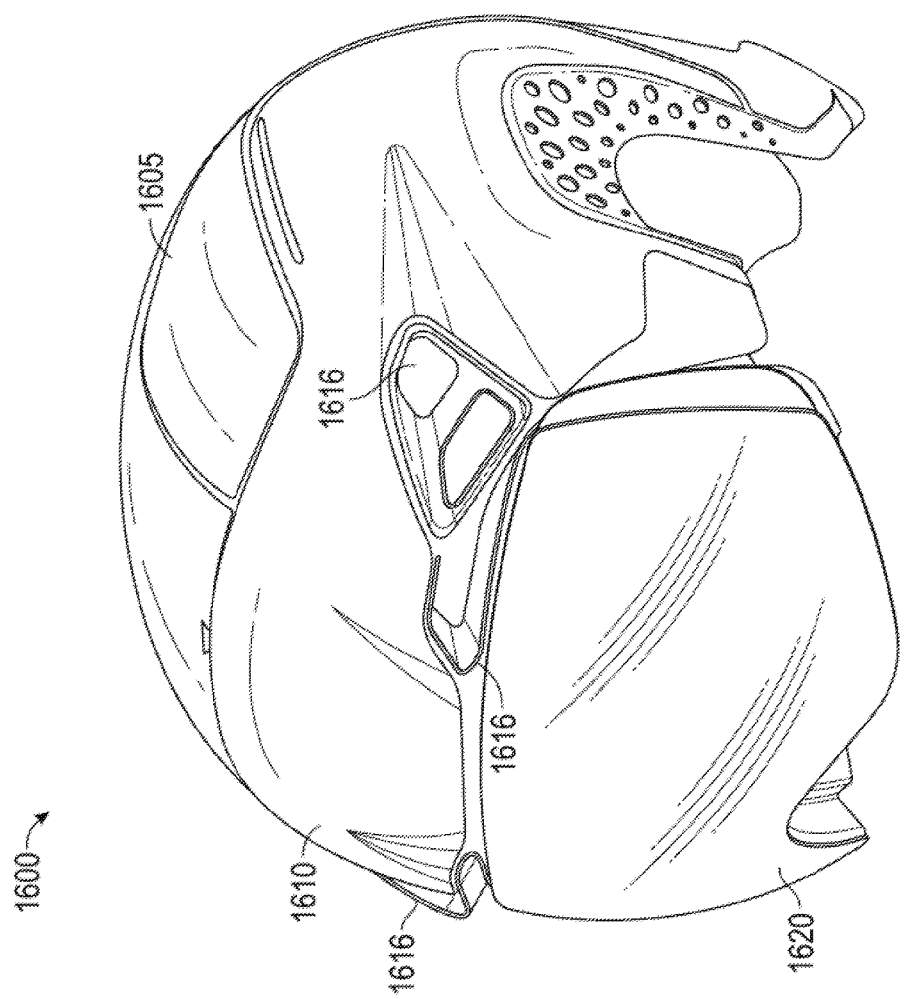
FIG. 3C illustrates another example of a helmet having eyewear including an embodiment of a lens.

FIGS. 3A-3C illustrate embodiments of helmets 1300, 1400, 1600 that can incorporate an embodiment of an anti-fogging lens, such as, for example, lens 102 or 104. FIG. 3A illustrates an example modular helmet having a base portion and an eyewear adapter module configured to attach to the base portion and to be tailored to eyewear, such as, for example, any of the eyewear disclosed herein.

FIG. 3A illustrates an example helmet 1300 having a base portion 1305 and an eyewear adapter module 1310 configured to attach to the base portion 1305 and to be tailored to eyewear, such as goggles, sunglasses, glasses, or other such eyewear. The eyewear adapter module 1310 is further configured to be adjustable after being attached to the base portion 1305. For example, the eyewear adapter module 1310 can be configured to be adjusted by sliding the eyewear adapter module 1310 down from the base portion 1305 towards the eyewear 1320. This advantageously allows the eyewear adapter module 1310 to interface more closely with the eyewear 1320.

Due at least in part to differences between users' heads and faces, the same eyewear would be positioned differently on the face of each user. The eyewear may be higher or lower on the head, for example. In addition, the positioning of a helmet on a head of the wearer will differ between different wearers. In some instances, a gap 1304 between the helmet 1300 and the eyewear 1320 can be at least about 0.25 inches and/or less than or equal to about 2 inches, at least about 0.5 inches and/or less than or equal to about 1.5 inches, or at least about 0.75 inches and/or less than or equal to about 1 inch. Even with the eyewear adapter module 1310, the gap 1304 may still persist for some users. Accordingly, even though the eyewear adapter module 1310 is tailored to the eyewear 1320, there may still be an undesirably large gap or space 1304 between the eyewear adapter module 1310 and the base portion 1305 of the helmet 1300 when worn by some users. The adjustable eyewear adapter module 1310 allows the user to adjust the position of the eyewear adapter module 1310 so that it can be positioned adjacent to the eyewear 1320. For example, the eyewear adapter module 1310 can be adjusted to reduce the gap 1304 between a bottom portion 1312 of the eyewear adapter module 1310 and a majority of a top portion 1322 of the eyewear 1320 to be less than or equal to about 0.5 inches, to be less than or equal to about 0.25 inches, to be less than or equal to about 0.125 inches, or to be in contact with one another.

As described herein, the eyewear adapter module 1310 can be positioned so that an interface between the eyewear adapter module 1310 and the eyewear 1320 provides one or more advantages. For example, a bottom portion 1312 of the eyewear adapter module 1310 can be adjusted until it contacts a majority of a top portion 1322 of the eyewear 1320. The bottom portion 1312 of the eyewear adapter module 1310 can be a surface of the eyewear adapter module 1310. The eyewear adapter module 1310 can be plastic, metal, rubber, TPE, foam, a combination of these or some other materials that are displaceable, compressible, and/or deflectable. In particular, the bottom surface 1312 can be displaceable, compressible, and/or deflectable to facilitate contact between a majority of the bottom surface 1312 and a majority of the top surface 1322 of the eyewear 1320. The bottom surface 1312 can include securing mechanisms such as adhesives, loop-and-hook material, snaps, magnets, or the like so that the eyewear adapter module 1310 remains substantially attached to the eyewear 1320 during use. The top portion 1322 of the eyewear 1320 can similarly be a rigid edge or surface of the eyewear 1320 or it can include foam, rubber, plastic, TPE, or the like as well. The eyewear 1320 can be configured to include securing mechanisms such as adhesives, hook-and-loop material, snaps, magnets, or the like that are compatible with the eyewear adapter module 1310 to help secure the eyewear adapter module 1310 in position against the eyewear 1320.

In some embodiments, the eyewear adapter module 1310 includes a locking mechanism that secures the eyewear adapter module 1310 substantially in place relative to the base portion 1305. For example, a friction-based locking device can be engaged to increase the friction between the eyewear adapter module 1310 and the base portion 1305 so that it becomes more difficult to move the eyewear adapter module 1310. As another example, a ratchet locking device can be engaged to lock the eyewear adapter module 1310 in place. As another example, a locking device can be used to limit movement of the eyewear adapter module 1310 to a certain point (e.g., in the upward or downward direction), allowing a limited range of movement of the eyewear adapter module 1310 when the locking device is engaged. In certain embodiments, the eyewear adapter module 1310 can be adjusted, locked, and unlocked without the use of tools (e.g., by hand).

FIG. 3B illustrates another example of an adjustable eyewear adapter module 1410 attached to a base portion 1405 of a helmet 1400. The adjustable eyewear adapter module 1410 can slide down to engage with eyewear 1420 to close a gap between the eyewear 1420 and the base portion 1405. This sliding eyewear adapter module 1410 can be configured to adjust to multiple eyewear sizes and heights, allowing for a more generic eyewear adapter module 1410 that is not necessarily tailored to particular eyewear, but can be generic to more general eyewear designs. In addition, foam, rubber, TPE or other similar displaceable, compressible, and/or deflectable material can be included on the eyewear adapter module 1410 so that the material can contact the eyewear 1420 and close gaps between the eyewear adapter module 1410 and the eyewear 1420 that may arise due at least in part to differing surface contours.

FIG. 3C illustrates an example of an eyewear adapter module 1610 configured to provide venting for eyewear 1620 as used with a helmet 1600. The eyewear adapter module 1610 can be tailored for use with the eyewear 1620 to provide venting for the eyewear through the use of apertures 1616 in the eyewear adapter module 1610. The apertures 1616 can be configured to provide desirable or tailored air flow to reduce condensation or fogging in the eyewear 1620. The apertures 1616 can be configured to provide air flow to provide cooling for the wearer. For example, the apertures 1616 can be configured to generate a Venturi flow that generates a flow of air in the eyewear 1620 to assist in the removal of damp, warm air. Accordingly, the eyewear adapter module 1610 can be tailored for use with the eyewear 1620 to reduce or eliminate gaps between the eyewear 1620 and the helmet 1600 as well as provide tailored functionality for the helmet and eyewear combination, such as venting.

The eyewear adapter module 1610 can be configured to secure to an external surface of the base portion 1605, covering a substantial fraction of the base portion 1605. The eyewear adapter module 1610 can be configured to rotate around a pivot point to rotate into position relative to the eyewear 1620. Thus, the movement and positioning of the eyewear adapter module 1610 can be similar to a face shield of other helmets, except that the eyewear adapter module 1610 is configured to be a non-optical component and/or the eyewear adapter module 1610 is configured to not cross a line of sight of the wearer.

Example Anti-Fog Eyewear Configurations

FIG. 4A illustrates an example configuration of a laminated lens that resists accumulation of condensate thereon. The lens includes a proximal lens element 408 configured to be closer to the wearer's head and a distal lens element 424 configured to be further from the wearer's head when eyewear incorporating the lens is worn. The proximal lens element 408 and the distal lens element 424 are bonded by an adhesive layer 448 disposed between the lens elements.

In the illustrated embodiment, the proximal lens element 408 includes an anti-fog layer 440. The anti-fog layer 440 can comprise activated cellulose acetate propionate (CAP). The thickness of the anti-fog layer 440 is about 500 µm. The thickness can be selected such that the layer 440 is capable of absorbing sufficient moisture from the air between the proximal lens element 408 and the wearer's face to avoid the accumulation of condensate on the proximal surface of the laminated lens.

An interface layer 444 is disposed adjacent to the anti-fog layer 440. In FIG. 4A, the interface layer 444 is a substantially stoichiometric thin silicon dioxide layer deposited on the distal surface of the anti-fog layer by physical vapor deposition. Ion beam assisted deposition techniques can be used to control the oxidation state of the interface layer 444 comprising silicon dioxide. The thickness of the silicon dioxide layer 444 is about 20 nm. The interface layer 444 can function as a vapor barrier. One or more functional layers, such as, for example, electrochromic layer, a heating element, an airgap, etc. can be disposed on a side of the interface layer 444 as described herein. In some embodiments, the anti-fog layer 440 and the interface layer 444 can be attached to one or more functional layers, such as, for example, electrochromic layer, a heating element, an airgap, etc. with or without the use of adhesives.

In the illustrated embodiment, the distal lens element 424 includes a PET layer 456 that provides stiffness to the laminated lens. The PET layer has a thickness greater than or equal to about 0.2 mm and/or less than or equal to about 2 mm.

An ITO layer 452 is deposited on the proximal surface of the PET layer. The ITO layer 452 is in electrical communication with a silver busbar 450 that is configured to connect to a power supply through one or more metal contacts and/or electrical wires. For example, the silver busbar 450 can be connected to an electrical wire disposed on a distal side of the ITO layer 452 through a metal contact extending between the silver busbar 450, the ITO layer 452, and the PET layer 456. The thickness of the silver busbar 450 is about 15 µm to about 30 µm. When a power supply supplies electric current across the ITO layer 452 via the silver busbar 450, the temperature of the ITO layer 452 is increased via the mechanism of joule heating. The ITO layer 452 thereby heats the other layers of the laminated lens. In some embodiments, the heat supplied by the ITO layer 452 can evaporate accumulated condensate from the distal and/or proximal surfaces of the laminated lens. In some embodiments, the heat supplied by the ITO layer 452 can inhibit accumulation of condensate on the distal and/or proximal surfaces of the laminated lens. The thickness of the ITO layer is about 10 µm to about 100 µm.

The adhesive layer 448 bonds the proximal lens element 408 and the distal lens element 424 together. The adhesive layer 448 comprises optically clear adhesive and has a thickness of greater than or equal to about 30 μm, about 50 μm, and/or less than or equal to about 100 μm.

Figure 4B:
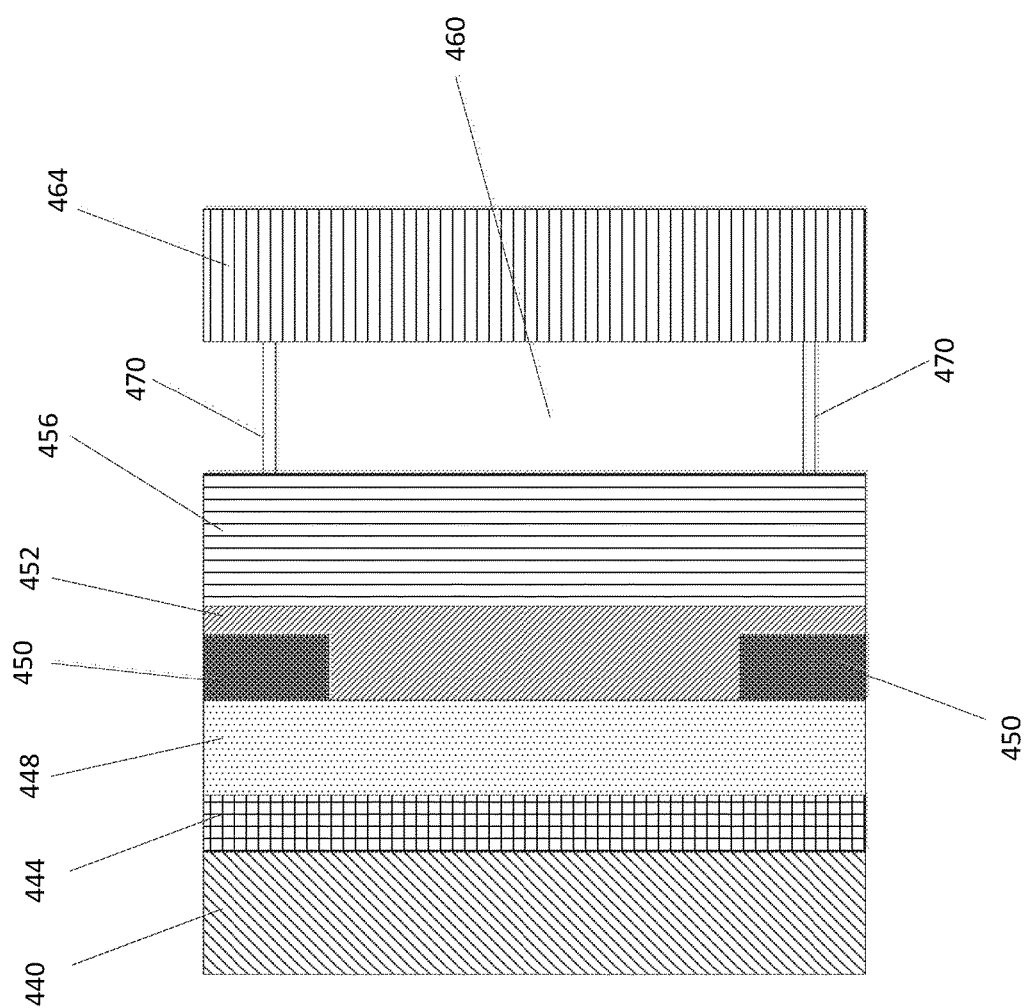
FIG. 4B illustrates an example lens configuration comprising the lens component shown in FIG. 4A spaced apart from a second component by spacers.

FIG. 4B illustrates an example lens configuration comprising the lens component shown in FIG. 4A spaced apart from a second lens component 464 by spacers 470. The spacers 470 can form a gap 460 between the lens components that can be filled with a thermally insulating material, such as, for example, air. The gap 460 can have a thickness greater than equal to about 0.5 mm and less than or equal to about 10 mm. The gap 460 can comprise an inert gas, such as, for example nitrogen. In some implementations, the gap 460 can be a vacuum. The spacers 470 can have any of the configurations described with reference to the spacers 206 shown in FIGS. 2A-2C. The spacers 470 can comprise foam gaskets with adhesives on both sides to adhere to the PET layer 456 and the second lens component 464. The second lens component 464 can be disposed distally from the first lens component and can have any of the configurations described with reference to the lens component 204 shown in FIGS. 2A-2C. The second lens component 464 can comprise a substrate (e.g., a polycarbonate or a polymer substrate) that is coated with a hard coat (HC). The substrate of the second lens component 464 can have a thickness greater than or equal to about 0.5 mm and less than or equal to about 5.0 mm.

Figure 4C:
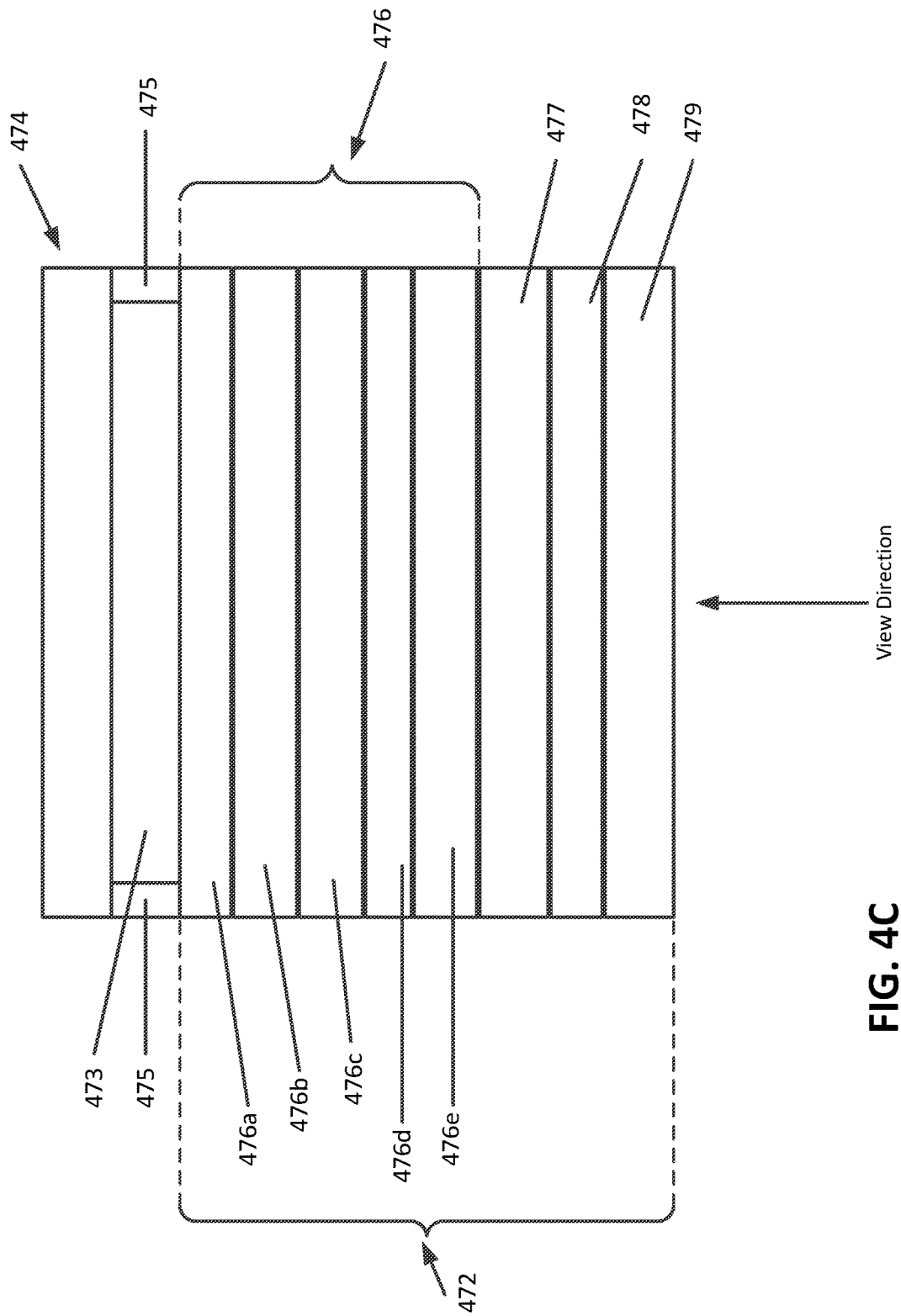
FIGS. 4C, 4D, and 4E illustrate example lens configurations comprising an anti-fog layer and an interface layer.

FIG. 4C illustrates an example configuration of a lens comprising an anti-fog layer and an interface layer. The lens can be a laminated lens. The lens comprises an anti-fog layer 479, an interface layer 478 and an electrochromic (EC) cell 476. As discussed herein, the interface layer 478 can facilitate adhesion of the anti-fog layer 479 to a functional layer, including. for example, to one or more layers of the EC cell 476. The interface layer 478 can facilitate adhesion of the anti-fog layer 479 to the functional layer including but not limited to the layers of the EC cell 476 by resisting delamination and remaining in substantial contact with the anti-fog layer 479 and the functional layer. The interface layer 478 can act as a moisture or vapor barrier and/or reduce the likelihood of delamination of the anti-fog layer 479 from other lens components as a result of exposure to high humidity, repeated temperature cycling, and/or other environmental stresses over a period of time.

The EC cell 476 comprises a layer of electrochromic material 476c sandwiched between a first electrically conductive layer 476b and a second electrically conductive layer 476d. The first electrically conductive layer 476b is disposed on a side of a first substrate 476a and the second electrically conductive layer 476d is disposed on a side of a second substrate 476e. The EC cell 476 can be attached to the vapor barrier 478 by an adhesive layer 477 disposed on a side of the second substrate 476e opposite the side on which the second electrically conductive layer 476d is disposed. The adhesive layer 477 can comprise an optically clear adhesive and/or a pressure sensitive adhesive (PSA). The anti-fog layer 479 can comprise an acetate (e.g., cellulose acetate propionate (CAP). The interface layer 478 can comprise an inorganic material, such as, for example, an oxide. In some embodiments, the oxide can be silicon dioxide. The first substrate 476a can be spaced apart from a lens component 474 by spacers 475. The spacers 475 can comprise foam gaskets with adhesives on both sides to attach to the first substrate 476a and the layer 474. The spacers 475 can form a gap 473 between the first substrate 476a and the lens component 474. The gap 473 can be a vacuum, comprise an inert gas (e.g., nitrogen), or be a consuming air gap. For example, the gap 473 can comprise a getter. As another example, the gap 473 can comprise material that reduces an amount of a gas, such as, for example, oxygen in the gap 473. The gap 473 can be configured to reduce or prevent oxidation of materials of the lens.

Figure 4D:
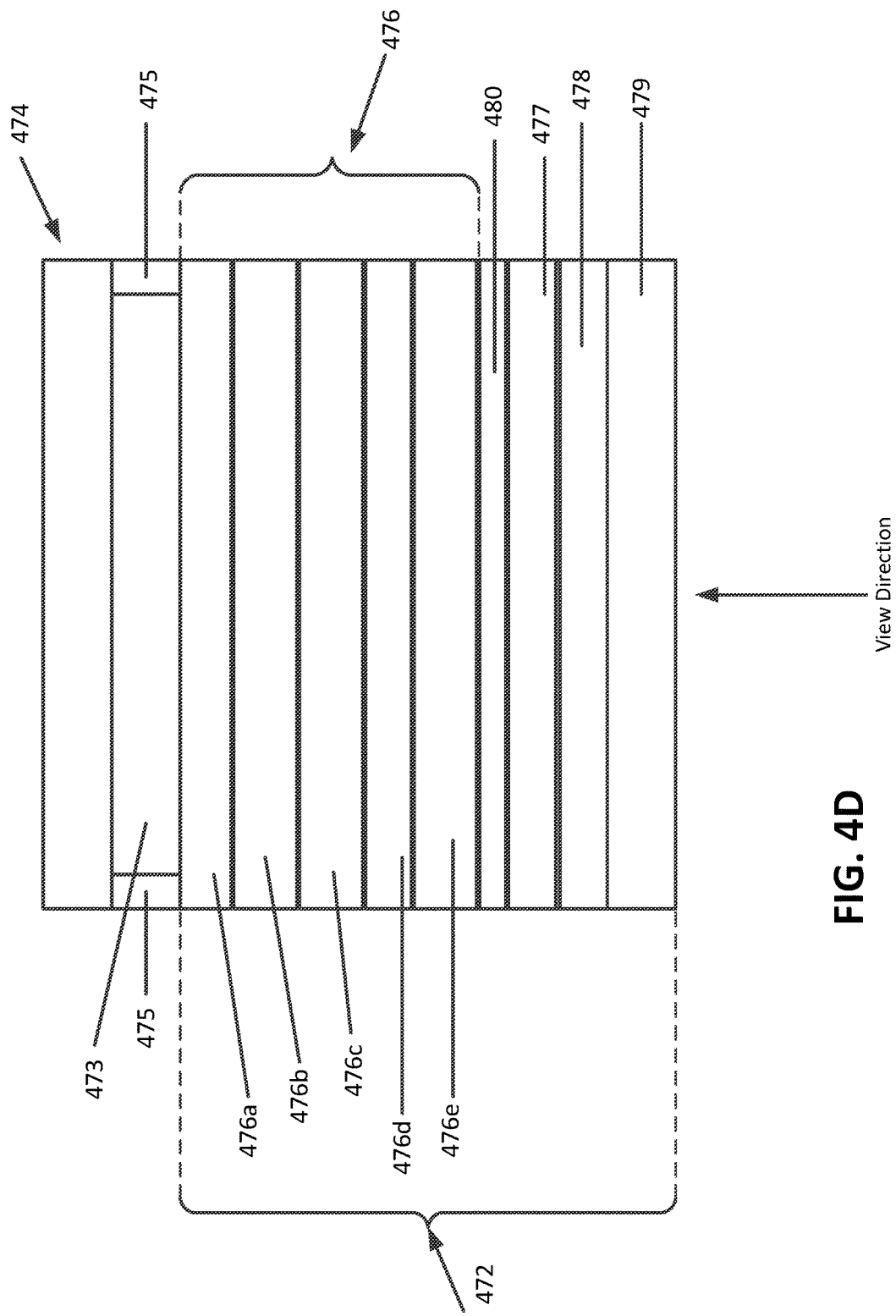

The lens component 474 can be configured as an outer (or distal) lens element that is configured to be further from the wearer's head when eyewear incorporating the lens is worn. The layers 476a-476e, 477, 478, and 479 can be configured as an inner (or proximal) lens element 472 configured to be closer to the wearer's head when eyewear incorporating the lens is worn. The lens component 474 can comprise a polymer substrate (e.g., a polycarbonate substrate) that is coated on one or both sides with a hard coat (HC). The lens component 474 can comprise one or more functional layers, such as, for example, anti-reflection coatings, anti-static coatings, oxide layers, adhesive layers, etc. In some implementations, the various layers 476a-476e, 477, 478 and 479 can be disposed sequentially without any intervening layers. However, in other implementations, one or more additional functional layers can be disposed between the various layers 476a-476e, 477, 478 and 479 depicted in FIG. 4C. For example, a third conductive layer 480 can be disposed between the EC cell 476 and the adhesive layer 477 as depicted in FIG. 4D. The third conductive layer 480 can function as a heating element by providing Joule heating when electric current flows there through.

Figure 4E:
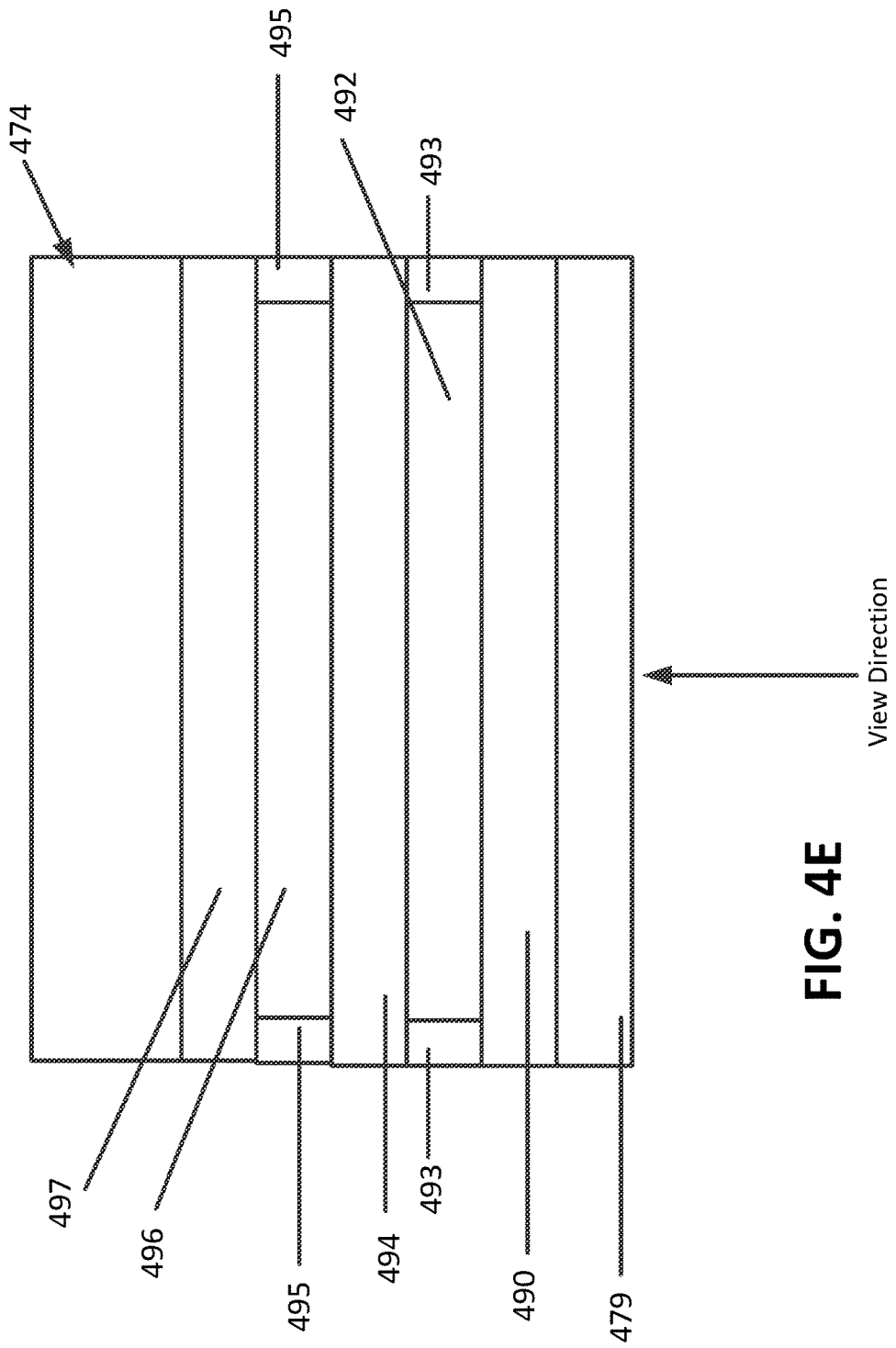

One or more surfaces of the interface layer can be in complete or partial contact with a lens component. In some embodiments, such contact area between the interface layer and the lens component is a majority of a facing surface of the interface layer, and in other embodiments, such contact area is a minority of a facing surface of the interface layer. For example, as illustrated in FIGS. 4C and 4D, the adhesive layer 477 contacts substantially an entire surface of the interface layer 478. However, as illustrated in FIG. 4E, a lens component (e.g., an adhesive layer and/or a spacer) can be in partial contact with the interface layer such that a gap is formed between the interface layer and the lens component. This is described in detail below with reference to FIG. 4E.

FIG. 4E illustrates an example configuration of a lens comprising a gap separating an interface layer from a functional layer. The lens can be a laminated lens. The lens comprises an anti-fog layer 479, a first interface layer 490 and a functional layer 494. The functional layer 494 is spaced apart from the interface layer 490 by a gap 492 formed by spacers 493 disposed over the first interface layer 490. The spacers 493 partially contact a surface of the first interface layer 490. The spacers 493 can be adhered to the first interface layer 490 by an adhesive (e.g., an optically clear adhesive, or a pressure sensitive adhesive). The adhesive can be at least partially incorporated with the spacers 493. The spacers 493 can comprise a gasket, foam, a polymer material, rubber material, or combinations thereof. The first interface layer 490 facilitates attachment of the anti-fog layer 479 to the functional layer 494 via the spacer 493. The interface layer 490 can facilitate adhesion of the anti-fog layer 479 to the functional layer 494 by resisting delamination and remaining in substantial contact with the anti-fog layer 479 and the spacer 493 even when exposed to moisture, environmental stresses and/or repeated temperature cycling or combinations thereof. The first interface layer 490 can function as a moisture barrier and improve adhesion of the anti-fog layer 479 to the first interface layer 490 and the spacer 493 to the first interface layer 490. Thus, the first interface layer 490 can improve adhesion between the anti-fog layer 479 and the functional layer 494 and reduce the likelihood of delamination when exposed to moisture, environmental stresses and/or repeated temperature cycling or combinations thereof. In certain embodiments, the first interface layer 490 resists delamination of the anti-fog layer 479 from other lens components. The first interface layer 490 can comprise one or more dielectric materials, one or more oxides (e.g., silicon dioxide), or another inorganic material with ceramic bulk properties. In some embodiments, the first interface layer 490 can be in contact with at least a substantial portion of the anti-fog layer 479. In certain embodiments, a lens comprises a lens component, an interface layer, and an anti-fog layer in sequence. The anti-fog layer and the first interface layer 490 can be a part of an inner or proximal lens element that is disposed closer to the wearer's head.

With continued reference to FIG. 4E, the gap 492 can be a vacuum. The gap 492 can comprise an inert gas (e.g., nitrogen), or be a consuming air gap. For example, the gap 492 can comprise a getter. As another example, the gap 492 can comprise material that reduces an amount of a gas, such as, for example, oxygen in the gap 492. The gap 492 can be configured to reduce or prevent oxidation of the various layers of the lens.

The functional layer 494 can comprise one or more layers, one or more coatings, one or more substrates, one or more laminates or a combination thereof. The functional layer 494 can include color enhancement filters, chroma enhancement filters, a laser attenuation filter, electrochromic filters, photoelectrochromic filters, variable attenuation filters, anti-reflection coatings, interference stacks, hard coatings, flash mirrors, anti-static coatings, anti-fog coatings, electrically conductive materials, other functional layers, or a combination of functional layers. The functional layer 494 can be configured to provide color enhancement functionality, light attenuation functionality, electrochromic functionality, photochromic functionality, heating functionality, electrical conduction functionality, anti-reflection functionality, anti-static functionality, anti-fog functionality, scratch resistance, mechanical durability, hydrophobic functionality, reflective functionality, darkening functionality, aesthetic functionality including tinting, or any combination of these.

For example, the functional layer 494 can comprise the EC cell 476 comprising layers 476a-476e as described herein. As another example, the functional layer 494 can comprise a heating element comprising an electrically conductive layer that can provide Joule heating as described herein. Additional examples of the functional layer 494 that are configured to provide one or more functionalities are described in International Publication No. WO 2016/077431 and International Publication No. WO 2013/169987 both of which are incorporated by reference herein in their entirety for all that they disclose. Examples of color enhancement filters and/or chroma enhancement filters providing color enhancement, chroma enhancement and/or light attenuation functionalities are described in U.S. Pat. No. 8,770,749, U.S. Pat. No. 9,134,547 and U.S. Pat. No. 9,575,335 all of which are incorporated by reference herein in their entirety for all that they disclose.

The lens comprises a second interface layer 497 spaced apart from the functional layer 494 by a second gap 496 formed by spacers 495. The spacers 495 can be adhered to the second interface layer 497 by an adhesive (e.g., an optically clear adhesive, or a pressure sensitive adhesive). The adhesive can be at least partially incorporated with the spacers 495. The spacers 495 can comprise a gasket, foam, a polymer material, rubber material, or combinations thereof. It is noted from FIG. 4E that the spacers 495 only partially contact the second interface layer 497. The second interface layer 497 can facilitate adhesion of the spacers 495 to the second interface layer 497 by resisting delamination and remaining in substantial contact with the spacers 495. The second interface layer 497 can function as a moisture barrier and improve adhesion of the spacer 495 to the second interface layer 497. The second interface layer 497 can also advantageously maintain the attachment of the spacers 495 to the second interface layer 497 even when exposed to moisture, environmental stresses and/or repeated temperature cycling or combinations thereof.

The second interface layer 497 can facilitate attachment of one or more lens components of the lens disposed on a side of the second interface layer 497 that is opposite to the side on which the functional layer 494 is disposed. For example, a lens component 474 can be disposed over the second interface layer 497 on a side of the second interface layer 497 opposite the side on which the second gap 496 is disposed. The lens component 474 can comprise a polymer substrate (e.g., a polycarbonate substrate) that is coated on one or both sides with a hard coat (HC). The lens component 474 can comprise one or more adhesive layers, coatings, substrates, supports, spacers or combinations thereof. The lens component 474 can comprise one or more functional layers, such as, for example, color enhancement filter, chroma enhancement filter, a laser attenuation filter, electrochromic cell, electrochromic filter, photoelectrochromic filter, variable attenuation filter, anti-reflection coating, interference stack, hard coating, flash mirror, anti-static coating, anti-fog coating, electrically conductive material, or combinations thereof. The second interface layer 497 can facilitate adhesion of the lens component 474 to other layers and/or lens components. As discussed herein, the second interface layer 497 can resist delamination and remain in substantial contact with the lens component 474. The second interface layer 497 can provide several benefits, such as, for example, provide structural stability, function as a moisture or vapor barrier, reduce the likelihood of delamination of the various lens components when exposed to moisture, environmental stresses and/or repeated temperature cycling or combinations thereof. The second interface layer 497 can comprise one or more dielectric materials, one or more oxides (e.g., silicon dioxide), or an inorganic material with ceramic bulk properties.

The second gap 496 can be a vacuum, comprise an inert gas (e.g., nitrogen), or be a consuming air gap. For example, the second gap 496 can comprise a getter. As another example, the second gap 496 can comprise material that reduces an amount of a gas, such as, for example, oxygen in the second gap 496. The second gap 496 can be configured to reduce or prevent oxidation of various layers of the lens.

The lens component 474 can be at least partially incorporated into an outer (or distal) lens element that is configured to be further from the wearer's head when eyewear incorporating the lens is worn. The anti-fog layer 479 and the first interface layer 490 can be at least partially incorporated into an inner (or proximal) lens element that is configured to be closer to the wearer's head when eyewear incorporating the lens is worn.

One or more functional layers, such as, for example, anti-reflection coatings, electrically conductive layers, optical filters, etc. can be disposed between the various layers shown in FIGS. 4C-4E. For example, one or more functional layers, such as, for example, anti-reflection coatings, electrically conductive layers, optical filters, etc. can be disposed between the interface layer 478 and the anti-fog layer 479 described in FIGS. 4C-4D. As yet another example, an electrically conductive layer may be disposed between the interface layer 490 described in FIG. 4E and the gap 492. As yet another example, an electrically conductive layer may be disposed between the functional layer 494 and the gap 492 and/or the functional layer 494 and the gap 496 in FIG. 4E. It is noted that while an adhesive layer (e.g., adhesive layer 477) can be provided on one or both sides of the interface layer 478, interface layer 490 and/or interface layer 497, in various embodiments, no adhesive layer is provided on either side of the interface layer 478, interface layer 490 and/or interface layer 497.

Example Methods for Making Laminated Lenses

Figure 5A:
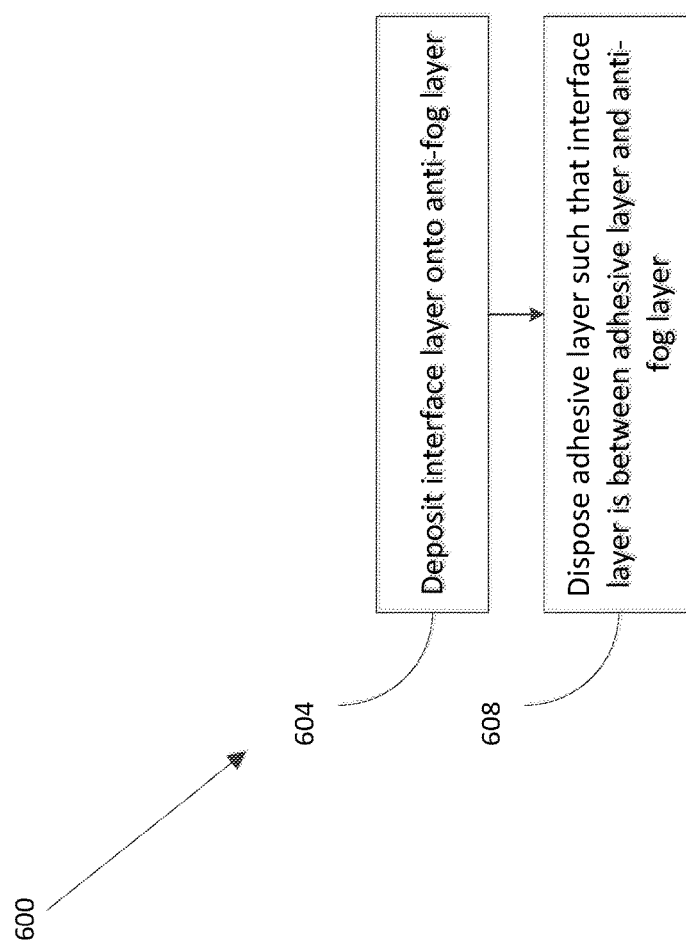
FIG. 5A illustrates an example method for manufacturing an anti-fog lens element.

FIG. 5A illustrates an example manufacturing method 600 for making an anti-fog lens element of a laminated lens, such as one of the lenses elements described with respect to the lens configurations 100, 150, the spectacles 118, the goggle 250, the helmets 1300, 1400, 1600, etc. The method 600 includes depositing 604 an interface layer onto an anti-fog layer. The anti-fog layer can have a thickness of 100 µm to 1000 µm or about 500 µm. A vapor deposition process can be used to deposit a thin layer of inorganic material having ceramic bulk properties having a thickness of 1 nm to 100 nm, 5 nm to 20 nm, or about 20 nm onto the anti-fog layer. The vapor deposition process can employ ion beam assisted deposition to control the oxidation state and/or microstructure of the inorganic material. The anti-fog layer is configured to resist accumulation of condensate on a proximal surface of the lens when the eyewear is worn. The interface layer can comprise amorphous or microcrystalline mineral oxide, such as, for example, silica glass or stoichiometric silicon dioxide, or a chalcogenide material. The interface layer and the anti-fog layer are part of a first lens element.

The method 600 includes disposing 608 an adhesive layer on the first lens element. The adhesive layer is configured to adhere to adjacent layers of the laminated lens. The adhesive layer is an optically clear adhesive having a thickness of 10 µm to 300 µm, 30 µm to 100 µm, or about 50 µm. The interface layer is positioned between the anti-fog layer and the adhesive layer when the adhesive layer is disposed on the first lens element.

In some embodiments, disposing 608 an adhesive layer is performed after depositing 604 an interface layer. In some embodiments, the steps of depositing 604 and interface layer and disposing 608 an adhesive layer are performed sequentially.

Figure 5B:
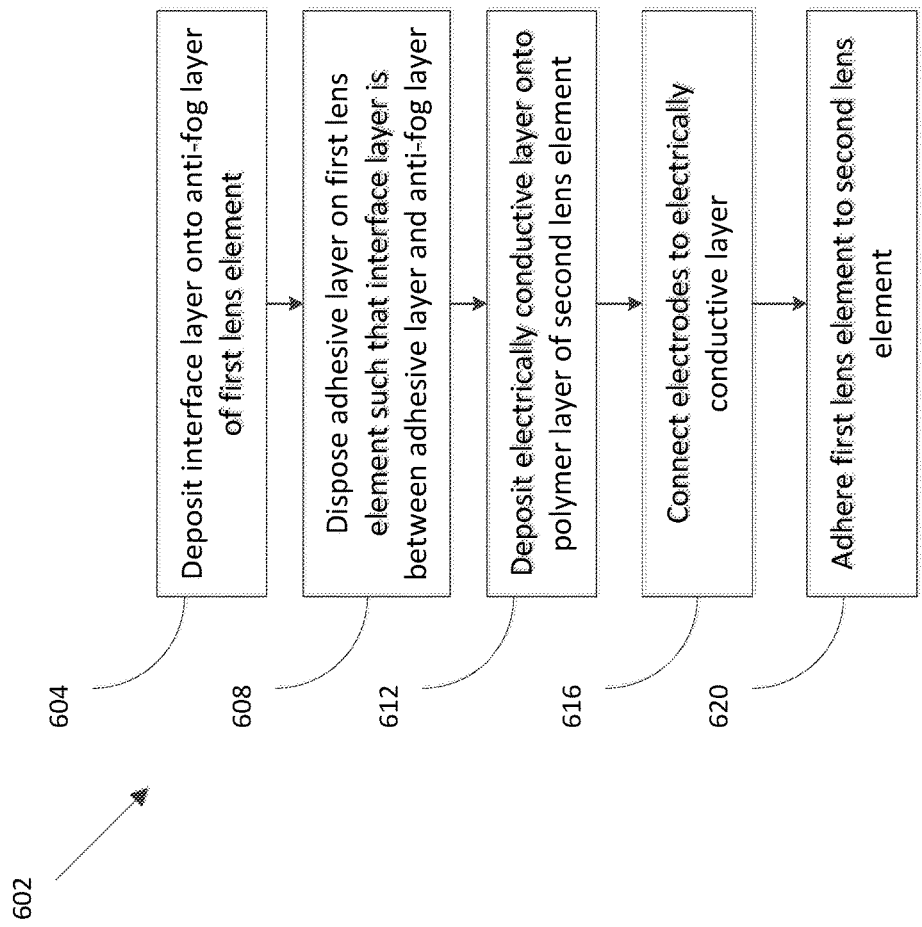
FIG. 5B illustrates an example method for manufacturing a laminated lens with anti-fogging functionality.

FIG. 5B illustrates an example manufacturing method 602 for making a laminated lens with anti-fogging functionality. In the illustrated embodiment, the method 602 includes the steps 604, 608 of the method 600 shown in FIG. 5A and includes additional steps. The method 602 further includes depositing 612 an electrically conductive layer configured to conduct electric current onto a polymer layer configured to stiffen the lens. The electrically conductive layer and polymer layer can generally have any of the configurations of such layers disclosed herein. The polymer layer and the electrically conductive layer are part of a second lens element.

The method 602 includes connecting 616 one or more electrodes to the electrically conductive layer. The electrodes can generally have any of the configurations of such electrodes disclosed herein. A power supply can be connected to the electrodes in order to supply electric current to the electrically conductive layer.

The method 602 includes adhering 620, with the adhesive layer, the first lens element to the second lens element. In some embodiments, the resulting laminated lens has substantially effective anti-fogging functionality and resists delamination, even when the lens is subjected to repeated temperature cyclings and/or repeated exposure to moisture. In some embodiments, the laminated lens is thermoformed to create a laminated lens with a desired curvature. In certain embodiments, the step of thermoforming does not create crazing or cracking in any of the lens layers.

In some embodiments, connecting 616 one or more electrodes is performed after depositing 612 an electrically conductive layer. In some embodiments, adhering 620 the first lens element to the second lens element is performed after connecting 616 one or more electrodes. In some embodiments, any two or more than two of the steps of the method 602 are performed sequentially in the order shown in FIG. 5B.

CONCLUSION

The embodiments of eyewear with laminated lenses and methods for making laminated lenses discussed above are examples and are thus not limiting. Without any loss of generality, the thicknesses of lens layers, order of lens layers, and/or order of method steps can be different from those depicted and described. Embodiments of laminated lenses including lens layers as described above can include one or more components that serve various functions within the lens. In some embodiments, one or more components of the lenses can provide additional functionality such as optical filtering, polarization control, photochromism, electrochromism, photoelectrochromism and/or partial reflection or absorption of incoming visible light, chroma enhancement, color enhancement, color alteration, or any combination of these. In some embodiments, one or more components of the lenses can provide mechanical protection, reduce stresses within the lens, and/or improve bonding or adhesion among the lens components. In some embodiments, the lenses can include components that provide additional functionality such as, for example, anti-reflection functionality, anti-static functionality, anti-fog functionality, scratch resistance, mechanical durability, hydrophobic functionality, hydrophilic functionality, reflective functionality, darkening functionality, aesthetic functionality including tinting, or any combination of these.

The particular features, structures, or characteristics of any embodiments discussed herein can be combined in any suitable manner in one or more separate embodiments not expressly illustrated or described. In many cases, structures that are described or illustrated as unitary or contiguous can be separated while still performing the function(s) of the unitary structure. In many instances, structures that are described or illustrated as separate can be joined or combined while still performing the function(s) of the separated structures. It is further understood that the lenses disclosed herein can be used in at least some configurations besides eyewear.

Various combinations or subcombinations of the specific features and aspects of the embodiments disclosed above may be made and still fall within one or more of the inventions. The disclosure herein of any particular feature, aspect, method, property, characteristic, quality, attribute, element, or the like in connection with an embodiment can be used in all other embodiments set forth herein. Accordingly, various features and aspects of the disclosed embodiments can be combined with or substituted for one another in order to form varying modes of the disclosed inventions. Thus, it is intended that the scope of the present inventions herein disclosed should not be limited by the particular disclosed embodiments described above.

While the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication.

The ranges disclosed herein encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. Features of embodiments disclosed herein preceded by a term such as "approximately", "about", and "substantially" as used herein represent the feature with some variability that still performs a desired function or achieves a desired result for that feature.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced embodiment recitation is intended, such an intent will be explicitly recited in the embodiment, and in the absence of such recitation no such intent is present. For example, as an aid to understanding, the disclosure may contain usage of the introductory phrases "at least one" and "one or more" to introduce embodiment recitations. However, the use of such phrases should not be construed to imply that the introduction of an embodiment recitation by the indefinite articles "a" or "an" limits any particular embodiment containing such introduced embodiment recitation to embodiments containing only one such recitation, even when the same embodiment includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce embodiment recitations. In addition, even if a specific number of an introduced embodiment recitation is explicitly recited, those skilled in the art will recognize that such recitation should typically be interpreted to mean at least the recited number (e.g., the bare recitation of "two recitations," without other modifiers, typically means at least two recitations, or two or more recitations).

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, embodiments, or drawings, should be understood to contemplate the possibilities of including one of the terms, either of the terms, or both terms. For example, the phrase "A or B" will be understood to include the possibilities of "A" or "B" or "A and B."

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Thus, it is intended that the scope of the inventions herein disclosed should not be limited by the particular embodiments described above, but should be determined by a fair reading of the claims.

The following is claimed:

1. A lens for eyewear comprising:
   an anti-fog layer configured to resist accumulation of condensate, wherein the anti-fog layer comprises a hydrophilic material, wherein the anti-fog layer is proximal to a wearer when the eyewear is worn;
   an interface layer comprising an inorganic material with ceramic bulk properties; and
   a lens component, wherein the interface layer is configured to facilitate attachment of the anti-fog layer to the lens component.

2. The lens of claim 1, wherein the hydrophilic material comprises cellulose acetate propionate.

3. The lens of claim 1, wherein the interface layer comprises silicon dioxide.

4. The lens of claim 1, wherein the lens component comprises a functional layer, wherein the functional layer comprises at least one of an electrically conductive layer, an electrochromic layer, a photochromic layer, a color filter, or a light attenuation filter.

5. The lens of claim 4, wherein the functional layer comprises an electrically conductive layer configured to conduct electric current when a power supply is electrically connected to the electrically conductive layer via one or more electrodes.

6. The lens of claim 5, wherein the electrically conductive layer comprises indium tin oxide.

7. The lens of claim 5, wherein the electrically conductive layer is disposed over a polymer layer configured to stiffen the lens.

8. The lens of claim 4, wherein the functional layer comprises an electrochromic layer.

9. The lens of claim 1, wherein the lens component comprises an adhesive layer disposed over the interface layer such that the interface layer is between the adhesive layer and the anti-fog layer, wherein the adhesive layer has a luminous transmittance greater than or equal to 50% using CIE Illuminant D65.

10. The lens of claim 1, wherein the lens component comprises one or more spacers configured to provide a gap between the interface layer and the lens component.

11. The lens of claim 10, wherein the gap comprises air, an inert gas or a getter.

12. The lens of claim 10, wherein the one or more spacers comprise an adhesive.

13. The lens of claim 1, further comprising a proximal lens element and a distal lens element spaced apart from the proximal lens element, the proximal lens element comprising the anti-fog layer, the interface layer, and the lens component.

14. Eyewear comprising a frame and the lens of claim 1 attached to the frame.

15. The eyewear of claim 14, wherein the eyewear is a goggle comprising:
a head strap configured to secure the goggle to a head of the wearer,
wherein the frame comprises a goggle frame comprising:
a central portion; and
a bridge disposed at the central portion, the bridge comprising a nosepiece section, and
wherein the goggle frame comprises one or more recesses adapted to hold the lens within a field of view of the wearer.

16. A helmet comprising the eyewear of claim 14, wherein the frame attaches to a base portion of the helmet, wherein the base portion is configured to absorb or distribute force from an impact, and wherein the eyewear is releasably attachable to the base portion.

17. The lens of claim 1, wherein the anti-fog layer has a thickness between 100 to 1000 μm, and wherein the interface layer has a thickness between 1 nm to 1000 nm.

18. A laminated anti-fog lens for eyewear comprising:
a first lens element comprising:
an anti-fog layer configured to resist accumulation of condensate on a proximal surface of the first lens element, wherein the anti-fog layer comprises a hydrophilic material, wherein the anti-fog layer is proximal to a wearer when the eyewear is worn, and wherein the anti-fog layer has a thickness of 100 μm to 1000 μm;
an interface layer having a thickness between 1 nm and 100 nm; and
a functional layer comprising an electrically conductive layer, the functional layer configured to conduct electric current when a power supply is electrically connected to the electrically conductive layer via one or more electrodes and generate Joule heating when electric current flows therethrough, wherein the interface layer is disposed between the anti-fog layer and the functional layer; and
a second lens element comprising a polymer layer, the second lens element spaced apart from the first lens element by a gap.

19. The lens of claim 18, wherein the hydrophilic material comprises cellulose acetate propionate.

20. The lens of claim 19, wherein the interface layer comprises silicon dioxide, and wherein at least a portion of the interface layer is in contact with at least a portion of the anti-fog layer.

21. The lens of claim 18, further comprising an adhesive layer between the interface layer and the functional layer, wherein the adhesive layer has a luminous transmittance greater than or equal to 50% using CIE Illuminant D65.

22. The lens of claim 18, wherein the gap comprises air or an inert gas.

23. The lens of claim 18, further comprising a second functional layer, the second functional layer comprising an electrochromic layer.

24. A lens for eyewear comprising:
a first lens element comprising:
an anti-fog layer configured to resist accumulation of condensate on a proximal surface of the first lens element; and
an interface layer comprising an inorganic material with ceramic bulk properties; and
an adhesive layer configured to adhere to adjacent layers of the lens, wherein the interface layer is disposed between the anti-fog layer and the adhesive layer.

25. The lens of claim 24, further comprising:
a second lens element comprising:
an electrically conductive layer configured to conduct electric current; and
a polymer layer configured to stiffen the lens;
wherein the adhesive layer is disposed between the first lens element and the second lens element.

26. The lens of claim 24, further comprising:
a second lens element comprising a functional layer, wherein the functional layer comprises at least one of an electrically conductive layer, an electrochromic layer, a photochromic layer, a color filter, or a light attenuation filter, and
wherein the adhesive layer is disposed between the first lens element and the second lens element.

27. The lens of claim 26, further comprising a proximal lens component and a distal lens component spaced apart from the proximal lens component by an insulating layer comprising a gas, wherein the proximal lens component comprises the first lens element, the second lens element, and the adhesive layer.

28. The lens of claim 24, wherein the anti-fog layer comprises cellulose acetate propionate.

29. The lens of claim 24, wherein the anti-fog layer has a thickness of 100 μm to 1000 μm, and wherein the interface layer has a thickness of 1 nm to 100 nm.

30. The lens of claim 24, wherein the interface layer comprises chalcogenide glass or mineral oxide glass.

31. The lens of claim 24, wherein the interface layer is a nanoscale composite comprising the inorganic material present in a matrix of organic material.

32. The lens of claim 24, wherein the adhesive layer comprises optically clear adhesive having a luminous transmittance greater than or equal to 50% using CIE Illuminant D65, wherein the adhesive layer has a thickness between 10 μm and 300 μm.

33. The lens of claim 24, wherein the adhesive layer covalently bonds to the first lens element and a second lens element.

* * * * *

UNITED STATES PATENT AND TRADEMARK OFFICE
CERTIFICATE OF CORRECTION

PATENT NO. : 10,295,821 B2
APPLICATION NO. : 15/679872
DATED : May 21, 2019
INVENTOR(S) : Brock Scott McCabe Page 1 of 1

It is certified that error appears in the above-identified patent and that said Letters Patent is hereby corrected as shown below:

In the Claims

In Column 33, Line 43, delete "100" and insert --100 µm--.

Signed and Sealed this
Fourteenth Day of January, 2020

Andrei Iancu
*Director of the United States Patent and Trademark Office*